US011399773B2

(12) United States Patent
Shanechi

(10) Patent No.: US 11,399,773 B2
(45) Date of Patent: Aug. 2, 2022

(54) STOCHASTIC-SWITCHED NOISE STIMULATION FOR IDENTIFICATION OF INPUT-OUTPUT BRAIN NETWORK DYNAMICS AND CLOSED LOOP CONTROL

(71) Applicant: UNIVERSITY OF SOUTHERN CALIFORNIA, Los Angeles, CA (US)

(72) Inventor: Maryam Shanechi, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 613 days.

(21) Appl. No.: 16/325,297

(22) PCT Filed: Aug. 14, 2017

(86) PCT No.: PCT/US2017/046829
§ 371 (c)(1),
(2) Date: Feb. 13, 2019

(87) PCT Pub. No.: WO2018/035067
PCT Pub. Date: Feb. 22, 2018

(65) Prior Publication Data
US 2019/0200934 A1 Jul. 4, 2019

Related U.S. Application Data

(60) Provisional application No. 62/375,385, filed on Aug. 15, 2016.

(51) Int. Cl.
*A61B 5/04* (2006.01)
*A61B 5/00* (2006.01)
(Continued)

(52) U.S. Cl.
CPC .......... *A61B 5/7246* (2013.01); *A61B 5/725* (2013.01); *A61B 5/7217* (2013.01);
(Continued)

(58) Field of Classification Search
CPC ..... A61B 5/7246; A61B 5/7217; A61B 5/725; G06F 30/20; A61N 1/36139; A61N 1/36064; A61N 1/36103; A61N 1/0534
See application file for complete search history.

(56) References Cited

U.S. PATENT DOCUMENTS

| 2007/0142873 | A1* | 6/2007 | Esteller | G16H 40/63 |
| | | | | 607/45 |
| 2013/0102919 | A1* | 4/2013 | Schiff | G16Z 99/00 |
| | | | | 600/544 |
| 2017/0043166 | A1* | 2/2017 | Choi | A61N 1/0534 |

FOREIGN PATENT DOCUMENTS

WO WO-2016168485 A1 * 10/2016 ......... A61N 1/36178

OTHER PUBLICATIONS

Yang, Yuxiao, and Maryam M. Shanechi. "A framework for identification of brain network dynamics using a novel binary noise modulated electrical stimulation pattern." 2015 37th Annual International Conference of the IEEE Engineering in Medicine and Biology Society (EMBC). IEEE, 2015 (Year: 2015).*

(Continued)

*Primary Examiner* — Christian Jang
(74) *Attorney, Agent, or Firm* — Snell & Wilmer LLP

(57) ABSTRACT

Time-efficient identification of a brain network input-output (IO) dynamics model for brain stimulation includes generating an input stochastic-switched noise-modulated waveform characterized by at least one parameter modulated according to a stochastic-switched noise sequence, inputting the input stochastic-switched noise-modulated waveform to a clinical brain-response system, recording one or more time-correlated outputs of the clinical brain-response system responsive to the input stochastic-switched noise-modulated waveform, and identifying a brain network IO dynamics model that optimally correlates the input stochastic-switched noise-modulated waveform to the one or more (Continued)

time-delimited outputs of the clinical brain-response system. A desired brain response to an input electrical signal may be obtained using the model, such as by modulating the input electrical signal using a closed-loop control algorithm based on the brain network IO dynamics model.

11 Claims, 27 Drawing Sheets

(51) Int. Cl.
    *A61N 1/36*     (2006.01)
    *G06F 30/20*     (2020.01)
    *A61N 1/05*     (2006.01)

(52) U.S. Cl.
    CPC ....... *A61N 1/0534* (2013.01); *A61N 1/36064* (2013.01); *A61N 1/36103* (2013.01); *A61N 1/36139* (2013.01); *G06F 30/20* (2020.01)

(56) References Cited

OTHER PUBLICATIONS

Brocker, David T., et al. "Improved efficacy of temporally non-regular deep brain stimulation in Parkinson's disease." Experimental neurology 239 (2013): 60-67 (Year: 2013).*
International Search Report and Written Opinion of the International Searching Authority (dated Jan. 11, 2018) for Corresponding International PCT Patent Application No. PCT/US17/46829, filed Aug. 14, 2017.
Brocker et al. "Improved Efficacy of Temporally Non-Regular Deep Brain Stimulation in Parkinson's Disease", Exp Neurol. Jan. 2013; 239: 60-67; abstract, p. 3, para 2, Fig. 1 and 2 Legends.
Yang et al. "A Framework for Identification of Brain Network Dynamics Using A Novel Binary Noise Modulated Electrical Stimulation Pattern"; Engineering in Medicine and Biology Society (EMBC), 2015 37$^{th}$ Annual International Conference of the IEEE; p. 2087-2090) (retrieved on Nov. 3, http://ieeexplore.ieee.org/abstract/document/7318799/?reload=true).'abstract, p. 2087, col. 1, para 1, p. 2088, col. 1, para 3, p. 2088, col. 2, para 2, para 4, p. 2089, col. 1, para 1, p. 2089, col. 2, para 3, p. 2090, col. 1, para 2, Fig. 3.

* cited by examiner

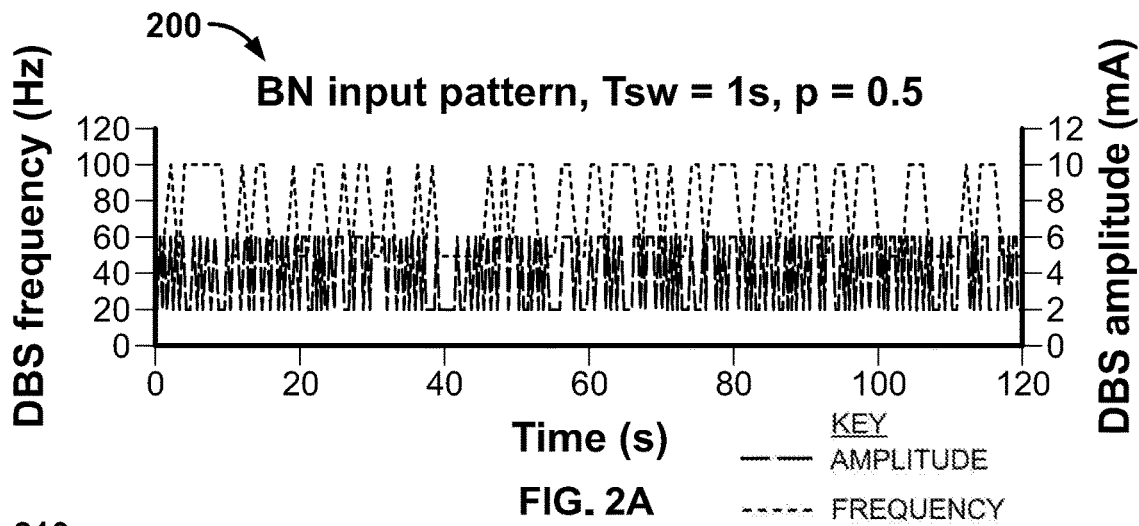
FIG. 2A
FIG. 2B
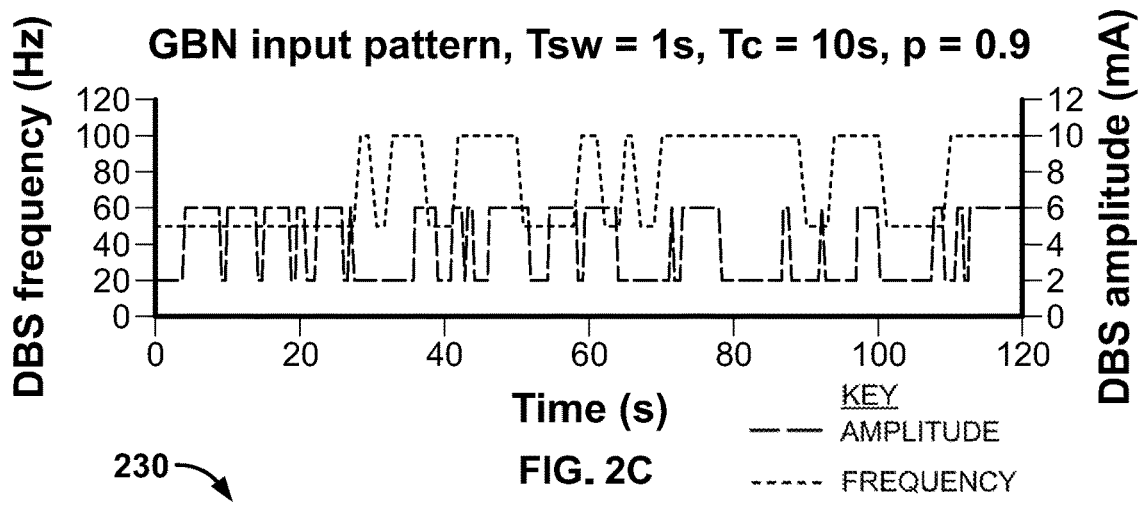
FIG. 2C
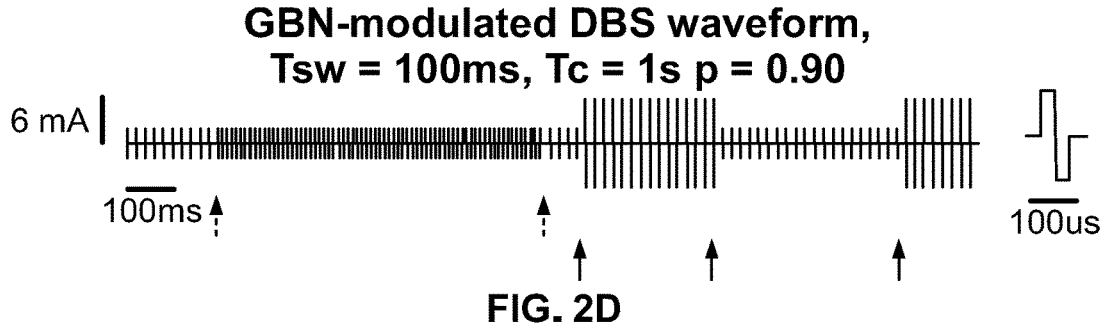
FIG. 2D

FIG. 3B   FIG. 3C

STOCHASTIC-SWITCHED NOISE STIMULATION FOR IDENTIFICATION OF INPUT-OUTPUT BRAIN NETWORK DYNAMICS AND CLOSED LOOP CONTROL

CROSS-REFERENCE TO RELATED APPLICATION

This application claims the benefit and priority of U.S. provisional patent application Ser. No. 62/375,385 filed Aug. 15, 2016, which is incorporated herein in its entirety by reference.

FIELD

The present disclosure relates to identification of input-output (I/O) brain network dynamics, and related applications in neuroscience and therapy, for example, deep brain stimulation for treatment of neurological disorders.

BACKGROUND

Millions of patients suffer from neurological disorders such as Parkinson's disease (PD), epilepsy and major depression. For patients who are refractory to traditional treatments such as medication, deep brain stimulation (DBS) provides an alternative treatment. DBS typically works by applying a periodic electrical pulse train stimulation to an electrode placed in an appropriate region of the brain, e.g., the subthalamic nucleus, to treat a certain neurological disorder, e.g., PD. DBS has been shown to effectively alleviate symptoms of advanced PD, refractory epilepsy, major depression, obsessive-compulsive disorder, and dystonia. Despite the clinical benefits of DBS, its widespread application is currently limited by its partial efficacy and potential side effects. For example, in PD, DBS treatments are commonly conducted in an open-loop and trial-and-error-based manner, whereby a clinician selects the appropriate DBS parameters such as frequency, amplitude and pulse width. It can take months for an expert to find initial effective DBS parameters via trial-and-error. Moreover, DBS parameters are only adjusted every few months to maximize clinical improvements while minimizing stimulation-induced side effects. However, symptom dynamics of PD can be much faster, which might have caused DBS to leave some clinical fluctuations partly uncontrolled.

Therefore, there has been extensive research on developing closed-loop or adaptive DBS systems for better treatment of PD and epilepsy. These studies suppose that neural signals such as local field potential (LFP) and neural spikings could represent the dynamics of the disorders and can be used as feedback to adjust the DBS treatment in closed loop. However, current closed-loop DBS systems for PD and epilepsy have only used simple on-off control schemes. These closed-loop DBS systems have two limitations. First, they only control the timing of the DBS pulse trains, i.e., when to start DBS and when to stop, but do not the pulse train amplitude and frequency during stimulation. For example, one study used an on-off control triggered by a threshold of LFP amplitude, but the effective DBS amplitude and frequency were still determined by experts in open loop. Second, even these simple on-off controllers have not been fully automated, e.g., determining the LFP amplitude threshold has been done by an expert via experience, without automatic optimization of treatment effect. While prototype closed-loop DBS systems have been shown to be more effective than standard open-loop DBS in both human clinical experiments and animal models, the above two limitations need to be addressed to allow for optimized wide-range clinical applications of closed-loop DBS systems. In addition, a principled system-identification framework capable of providing optimal or improved input-output (IO) dynamics estimation is currently lacking.

It would be desirable, therefore, to provide a time-efficient method for defining a model and model parameters capable of predicting the response of particular brain system to an input electrical signal and related therapeutic protocols that overcome these and other limitations of the prior art.

SUMMARY

This summary and the following detailed description should be interpreted as complementary parts of an integrated disclosure, which parts may include redundant subject matter and/or supplemental subject matter.

A common aspect of prior closed-loop DBS systems is a lack of model-based design. A "model-based design" of closed-loop DBS system or brain-machine interface (BMI) means a design that uses a computational model to quantify input-output (IO) dynamics of neural feedback signals in response to DBS parameters, and a closed-loop controller designed based on this model that optimizes the treatment effect. FIG. 1A shows a system 100 using a brain network IO dynamical model 102, output monitoring of neural activity $y_t$, and a closed loop controller 104 that generates electrical stimulation $u_t$ to achieve a specific therapeutic purpose based on a predictive brain model and real-time input $y_t$. Modeling and identification of network level I/O dynamics is essential for devising principled, high-performance closed-loop DBS controllers. The present disclosure teaches a general computational framework to identify brain network I/O dynamics and design model-based closed-loop DBS systems or brain-machine interfaces (BMIs) for treatment of a wide range of neurological disorders, or other applications.

Up until now, model-based closed-loop DBS systems have only been studied in simulations. For example, for treatment of tremor, a prior researcher built a linear autoregressive model to relate the input DBS amplitude to the output LFP waveform, and based on this model designed a minimum variance controller to regulate the LFP power spectrum to a reference profile derived under tremor free conditions. Simulation studies show the possibility of model-based controllers to control the DBS frequencies or amplitudes continuously to target desired neural firing rate pattern or LFP spectrum that represent a healthy state. However, one important topic that prior work has omitted is estimation of the network IO model parameters, or system-identification. The present inventors' prior work assumed perfect knowledge of the IO model parameters, or consisted of heuristic IO model identification without optimizing system-identification accuracy. Accurate identification of the IO dynamics has crucial influence on the performance of closed-loop controllers, and can be achieved using systems and methods as taught herein.

Closed-loop deep brain stimulation (DBS) systems can improve traditional open-loop DBS treatment of neurological disorders such as Parkinson's disease and depression by adjusting DBS parameters in real time based on neural feedback. However, current closed-loop DBS systems have not been model-based, and only used simple on-off control strategies that may not have optimal treatment effects. The fundamental limitation is that current systems lack appropriate quantification of the input-output (IO) dynamics from input DBS parameters to output neural feedback signals.

Modeling and identification of such network-level IO dynamics is essential for devising principled, high-performance closed-loop DBS controllers.

The present disclosure concerns applications using a general computational framework to identify brain network IO dynamics and design model-based closed-loop DBS systems or brain-machine interfaces (BMIs) for treatment of a wide range of neurological disorders. The approach uses linear state-space models to describe brain network IO dynamics and design open-loop system-identification experiments to estimate the model parameters. A novel open-loop input DBS waveform—a pulse train modulated by binary noise (BN) DBS parameters—satisfies both optimality constraints for system-identification and safety constraints for clinical operation. We further extend the BN-modulated DBS waveform to a generalized BN (GBN)-modulated DBS waveform to reduce the identification time.

The disclosure further describes a clinical closed-loop simulation testbed with the Neuro Omega™ microelectrode recording and stimulation system. Using this realistic closed-loop testbed, the identification framework can be tested in closed-loop control simulations, for example, by observing mood symptom control in depression or other condition. Our simulation results show that BN-modulated DBS waveform enabled accurate IO dynamics identification, and that a closed-loop controller designed from BN-identified models can achieve tight control of mood symptoms. Steady-state and transient performance is not significantly different from a best unrealizable controller that can be derived from a true brain network model. The closed-loop control performance is robust to stochastic noises, unknown disturbances and stimulation artifacts. Finally, when identification time is limited, performance of BN-modulated DBS waveform can be further improved by GBN modulated DBS waveform by incorporating time-constant information of the underlying brain network. Our results have significant implications for developing future closed-loop DBS treatments of a wide range of neurological disorders.

In an aspect of the disclosure, a method for time-efficient identification of a brain network input-output dynamics model for brain stimulation includes generating an input stochastic-switched noise-modulated waveform characterized by at least one parameter modulated according to a stochastic-switched noise sequence. The stochastic-switched noise-modulated waveform may be, or may include, a binary waveform. The at least one parameter may be selected from frequency, amplitude, or pulse width. In an aspect, the stochastic-switched noise-modulated waveform may be generalized by a tunable parameter based on a ratio of a minimum switching time ($T_{sw}$) to a time constant ($T_c$) for the brain network IO model. For example, the tunable parameter is determined by $1-T_{sw}/T_c$. In another aspect, the method may include estimating a value of $T_c$ by applying an on-off input pattern to the clinical brain-response system in open loop mode and measuring a rise time for achieving a defined initial portion of a transition period. The defined initial portion may be defined, for example by 1/e. The estimating may further include repeating the applying and the measuring thereby obtaining multiple values of the rise time, and averaging the multiple values.

The method may further include inputting the input stochastic-switched noise-modulated waveform to a clinical brain-response system. The brain-response system may be an electronic system that simulates brain response with microelectrodes. In an alternative, or in addition, the brain-response system may be an electronic system that provides and optionally records an electrical response of an actual brain using microelectrodes or equivalent monitoring tools. For example, the brain-response system may include an electrode implanted in a living brain with the outputs measured by an electrode array.

The method may further include recording one or more time-correlated outputs of the clinical brain-response system responsive to the input stochastic-switched noise-modulated waveform. The method may further include identifying, as a brain network IO dynamics model for brain stimulation, a mathematical model that optimally correlates the input stochastic-switched noise-modulated waveform to the one or more time-delimited outputs of the clinical brain-response system. In an aspect, the mathematical model is a linear state-space model.

In another aspect of the disclosure, a method for causing a desired brain response to an input electrical signal includes providing an input electrical signal to a true brain system via at least one input electrode, detecting a response of the true brain system to the input electrical signal via at least one output electrode, comparing the response to a desired brain response; and modulating the input electrical signal, according to a closed-loop control algorithm based on a brain network IO dynamics model for brain stimulation developed by correlating a stochastic-switched noise-modulated waveform input to the true brain system output, until the response matches the desired brain response. In an aspect, the brain network IO dynamics model optimally correlates the input stochastic-switched noise-modulated waveform to the true brain system output. In other aspects, the desired brain response may mitigate a neuropathic condition, or heighten a brain performance parameter. The brain network IO dynamics model may be developed as described in more detail elsewhere herein.

In related aspects, an apparatus for any of the aforementioned purposes may include a hardware processor coupled to a memory and to a waveform generator, the memory holding instructions that when executed by the processor cause the apparatus to perform the operations of the methods as summarized above.

To the accomplishment of the foregoing and related ends, one or more examples comprise the features hereinafter particularly pointed out in the claims and fully described in the detailed description following the brief description of the drawings.

BRIEF DESCRIPTION OF THE DRAWINGS

The features, nature, and advantages of the present disclosure will become more apparent from the detailed description set forth below when taken in conjunction with the drawings, in which like element numerals are used to indicate like elements.

FIG. 2A is a diagram illustrating an example of a random binary noise (BN) input pattern for generating a DBS waveform.

FIG. 2B is a diagram illustrating an example of a biphasic BN pulse train with two adjustable parameters for use as a DBS waveform.

FIG. 2C is a diagram illustrating an example of a generalized binary noise (GBN) input pattern wherein the probability of frequency change is adjustable, for generating a DBS waveform.

FIG. 2D is a diagram illustrating an example of GBN-modulated pulse train for use as a DBS waveform.

FIG. 3B is a functional block diagram illustrating operational aspects of simulated ECoG generation by a computational component of the testbed.

FIG. 3C is a functional block diagram illustrating operational aspects of generating DBS parameters by another computational component of the testbed.

DETAILED DESCRIPTION

Figure 1A:
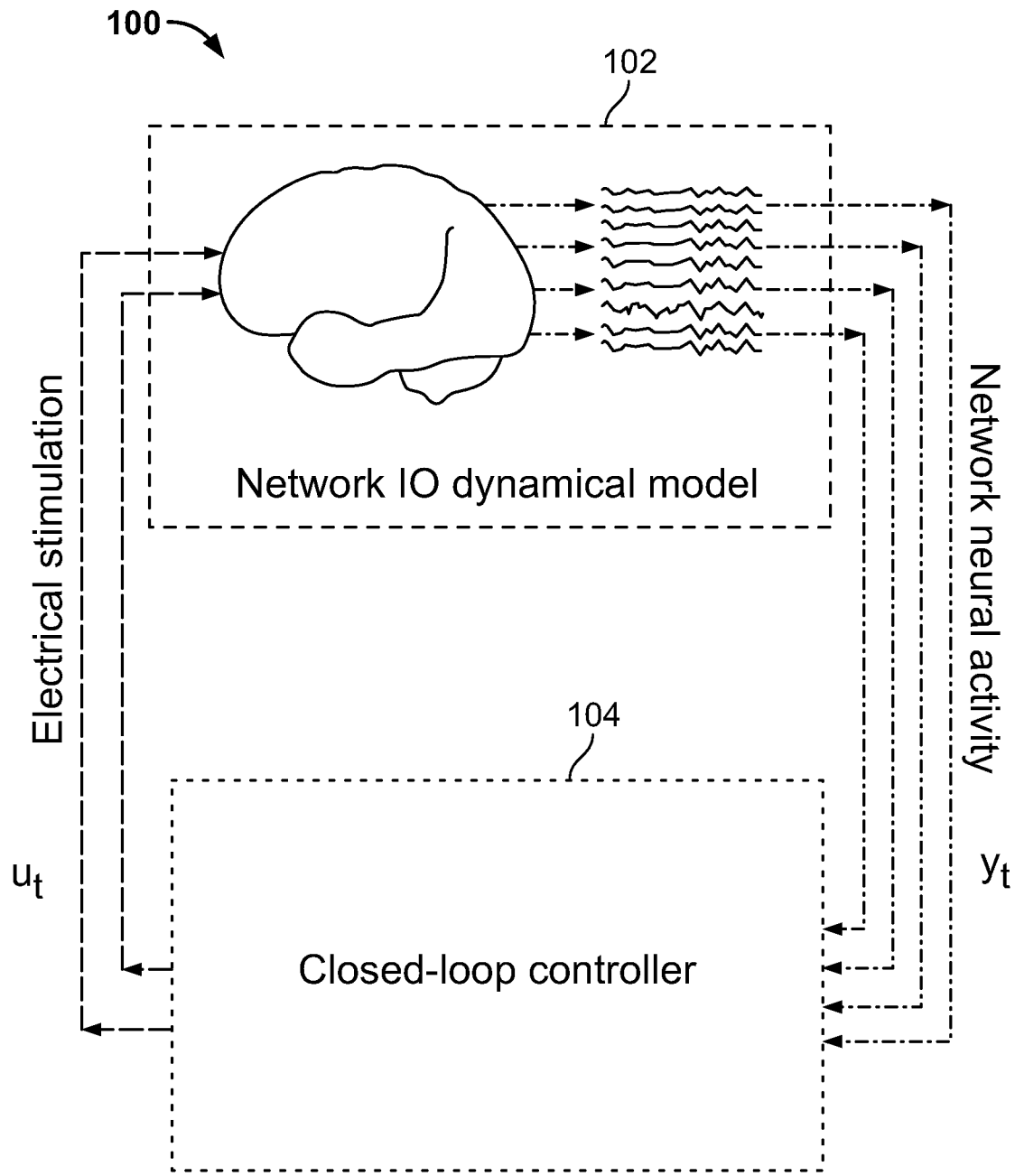
FIG. 1A is a block diagram showing components of a model-based closed loop controller for DBS.

A linear state-space model is used to describe brain network IO dynamics and design open-loop system-identification experiments to estimate the model parameters. A novel open loop input brain stimulation waveform—e.g., a pulse train modulated by binary noise (BN) DBS parameters—satisfies both optimality constraints for system-identification and safety constraints for clinical operation. The BN-modulated brain stimulation waveform is generalized to a generalized BN (GBN)-modulated stimulation waveform, reducing identification time and improving time efficiency. The brain stimulation waveform may be for deep brain stimulation (DBS).

The GBN is used as input to a clinical closed-loop simulation testbed with the Neuro Omega™ microelectrode recording and stimulation system. In a therapeutic application, the testbed is replaced by a true brain system with electrode inputs and outputs. Using this realistic closed-loop testbed or true brain system, parameters of the model for system operation are identified, for example, in an identification framework to build a closed-loop controller for mood symptom control in depression. After the closed loop controller is identified, closed loop control for the targeted brain state can be based on the identified BN waveform.

Simulation results show that the BN-modulated DBS waveform enabled accurate IO dynamics identification. A closed-loop controller designed from BN-identified models should be capable of achieving tight control of mood symptoms. Its steady-state and transient performance should be close to a best unrealizable controller that is derived assuming knowledge of a true brain network model. The closed-loop control performance of the model proved robust to stochastic noises, unknown disturbances and stimulation artifacts. When identification time is limited, performance of BN-modulated DBS waveform can be further improved by use of the GBN-modulated DBS waveform via incorporating the time-constant information of the underlying brain network. The results have significant implications for developing closed-loop DBS treatments for a wide range of neurological disorders, or other applications.

Design of the methods and apparatus as described herein may be based on a computational framework for identification of brain network IO dynamics, with the purpose of designing model-based DBS/stimulation controllers. A multiple-input-multiple-output (MIMO) linear state-space model (LSSM) is described for modeling the IO dynamics because LSSM (i) allows for efficient identification from possibly high-dimensional neural recordings, and (ii) is amenable to real-time and robust feedback-control. More detailed justifications of using LSSM are discussed later in the specification. With the model developed, LSSM parameters are identified by using open-loop system-identification experiments applying an appropriate input DBS waveform to stimulate the brain, and then collecting the input-output data to estimate LSSM parameters.

A crucial component of system identification is the choice of the input DBS waveform, which will critically influence the accuracy of model identification, and subsequently of closed-loop control. Therefore, optimal DBS input signals should be designed and applied for brain network IO identification. Current input DBS waveforms for brain network IO identification have only been chosen heuristically, without theoretical guarantees for optimality. For brain network IO identification, an optimal input design should at least satisfy the following constraints:
  (i) To ensure accurate IO identification, input waveforms should sufficiently excite the network neural activity so that maximal information is obtained from the IO data. For estimating LSSMs, this necessitates an input with white spectrum.
  (ii) To ensure clinical safety, input DBS waveforms should be constrained to take the form of pulse trains that are charge-balanced in short time intervals.
  (iii) An optimal input DBS waveform should be easy to implement in the DBS device.
  (iv) The input DBS waveform should allow for a short identification time since in typical clinical scenarios the time available for stimulation to perform system-identification is limited.

These constraints pose a challenging DBS/stimulation input design problem. The spectrum of traditional DBS pulse train waveforms is far from white. Even though pulse trains with Poisson arrivals (which are approximately "white") have been used to study brain's LFP under optogenetic stimulation, there exists no evidence that such waveforms are clinically safe and effective in electrical DBS. Accordingly, novel aspects of the present disclosure include a design for input DBS waveforms to solve the above constrained design problem for IO brain network identification with a LSSM model structure. The design provides a novel input DBS waveform that satisfies the optimal spectrum requirement, is clinically safe and is easy to implement. This DBS waveform is constructed as a pulse train whose parameters such as amplitude and frequency are stochastically changed according to a binary noise (BN) sequence. As used herein, this input DBS waveform may be referred to as a "BN-modulated" DBS waveform. In addition, to reduce system identification time, the BN-modulated DBS waveform may be extended to a generalized BN (GBN)-modulated DBS waveform by further estimating (using on-off stimulation) and incorporating in the waveform design the time-constant of the underlying brain network. This further optimizes BN to reduce identification time.

In addition, developing closed-loop DBS systems would significantly benefit from extensive and realistic simulations to verify performance and robustness before human experiments. However, so far, simulation studies for closed-loop DBS have been limited to running Monte Carlo experiments in a computer program, which makes modeling factors such as delays, recording noises, disturbances, and stimulation artifacts difficult. Accordingly, the present disclosure includes a clinical closed-loop simulation testbed within which modeling and closed-loop control strategies can be validated using the same recording and stimulation hardware that would be used in human experiments. The clinical real-time closed-loop simulation testbed uses the Neuro Omega™ microelectrode recording and stimulation system (Alpha Omega Co. USA Inc., Alpharetta, Ga.), and incorporates stochastic noises, disturbances, time-delays, and recording stimulation artifacts that are difficult to mimic purely using a computer program. This testbed fully resembles a clinical scenario except that the neural signal is generated by a simulated brain network. The testbed enables testing of both open-loop system-identification and closed-loop control.

Combined, the novel features summarized above allow testing of a novel modeling and identification framework for brain IO dynamics within a realistic clinical testbed using two sets of experiments. First, the framework is tested for open-loop system-identification by implementing the BN-modulated DBS waveform. It can be demonstrated thereby that the new input DBS waveform is critical for accurate estimation of the brain network IO model. In addition, the testbed enables accurate estimation of the time-scale of the underlying network, enabling in turn design of the new GBN-modulated DBS waveform to significantly reduce the identification time. Second, the framework can be tested by implementing it within the clinical testbed using a stochastically optimal linear-quadratic-Gaussian (LQG) closed-loop controller designed from the identified LSSM. Taking mood symptom control in depression as an example, it can be shown that the proposed modeling and identification framework using the BN-modulated DBS waveform is critical to achieve accurate closed-loop control of mood symptoms.

Network IO Dynamical Model and System Identification.

Figure 1B:
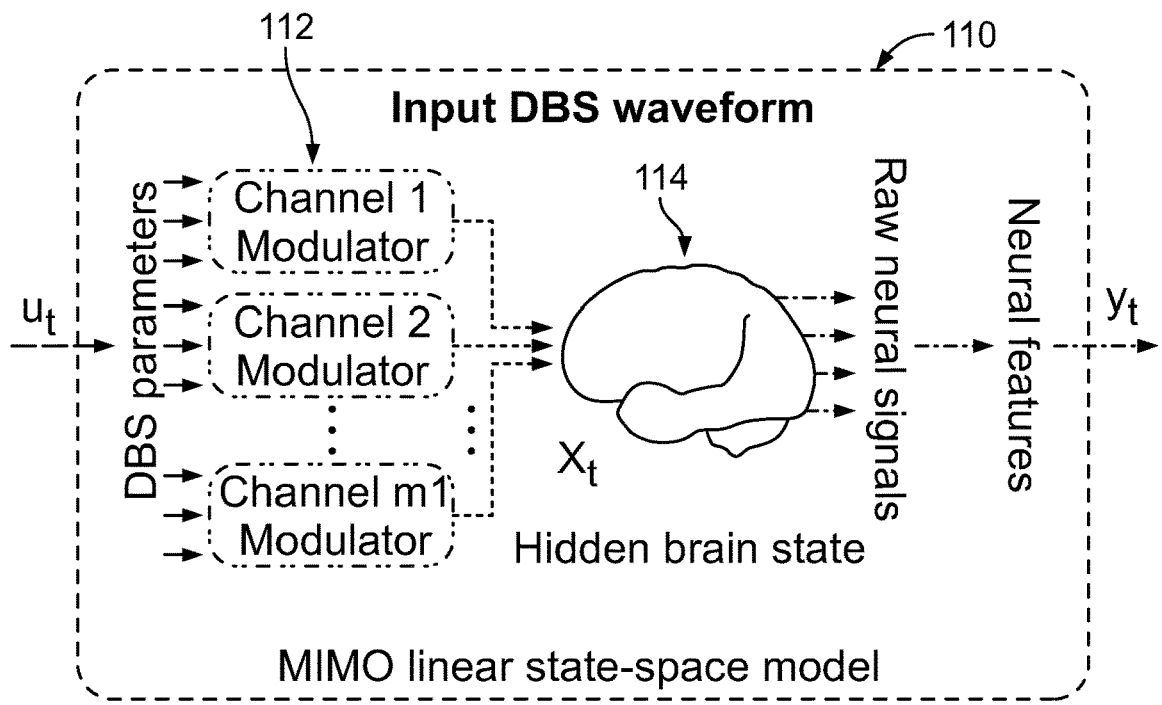
FIG. 1B is a block diagram showing components of a multiple input multiple output (MIMO) linear state space model (LSSM) for use in DBS closed loop control.

FIG. 1B shows aspects of a discrete time-invariant MIMO LSSM 110 to describe brain network IO dynamics for a hidden brain state 114. The MIMO LSSM may be based on a system of linear equations, for example:

$$x_{t+1} = Ax_t + Bu_t + w_t$$

$$y_t = Cx_t + Du_t + v_t \qquad (1)$$

In the system (1) and LSSM 110, $u_t \in \mathbb{R}^m$ represents the input electrical stimulation, $y_t \in \mathbb{R}^k$ represents the observed neural activity, and $x_t \in \mathbb{R}^n$ represents the hidden brain state 114. $w_t \in \mathbb{R}^n$ and $v_t \in \mathbb{R}^k$ are white Gaussian noises with zero mean to summarize modeling errors and unmeasured disturbances. The LSSM parameters are the model order n, the matrices $A \in \mathbb{R}^{n \times n}$, $B \in \mathbb{R}^{n \times m}$, $C \in \mathbb{R}^{k \times n}$ and $D \in \mathbb{R}^{k \times m}$, and the noise covariance defined as $$E\left[\begin{pmatrix} w_i \\ v_j \end{pmatrix}(w_i^T v_j^T)\right] = \begin{bmatrix} Q & S \\ S^T & R \end{bmatrix}\delta_{ij},$$

where $Q \in \mathbb{R}^{n \times n}$, $R \in \mathbb{R}^{k \times k}$, $S \in \mathbb{R}^{n \times k}$, and $\delta_{ij}=1$ if $i=j$ and 0 otherwise. The DBS parameters are used by the channel modulators 112 to producer multiple channels of the input electrical stimulation.

Pulse amplitude and frequency are important DBS parameters that can influence treatment outcomes of PD in open-loop simulation and clinical studies. Thus, the input $u_t$ may be defined as the DBS parameters, i.e., pulse frequency and amplitude, at each stimulation site for the brain. With $m_1$ stimulation sites, $u_t$ may have dimension $m=2m_1$. The input DBS waveform may be a continuous square pulse train 210 modulated by these DBS parameters, for example, as shown by FIG. 2B. As used herein, the DBS parameters $u_t$ may be referred to as an "input pattern", and the stimulation pulse train as "DBS waveform". The observed neural activity $y_t$ may be defined as the signal features associated with the neural recordings. Signal features may include, for example, firing rates of neural spikes, power spectrum of electrocorticography (ECoG), phase-amplitude-coupling of LFP, or any other useful feature. The symbol k denotes the total number of neural features used for model development and input control.

Figure 1C:
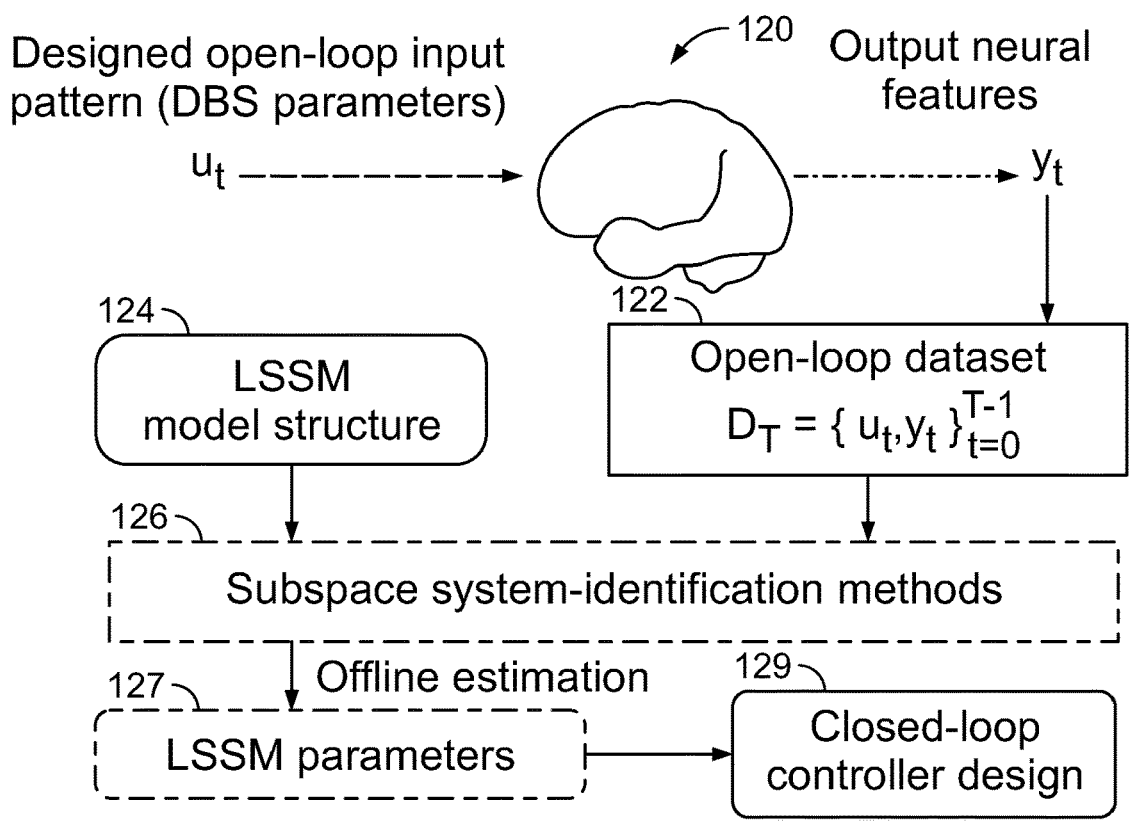
FIG. 1C is a diagram of a method for open-loop system-identification used for estimating parameters of an LSSM model.

LSSM parameters may be estimated by developing an open-loop system-identification approach 120 diagrammed in FIG. 1C. Critically, this system-identification requires the design of novel input patterns $\{u_t\}^T_{t=1}$ (where T is the duration of stimulation) to generate an informative open-loop DBS waveform. An open-loop IO dataset 122 $\mathcal{D}^T = \{u_t, y_t\}^T_{t=1}$ is collected based on the DBS waveform. The open-loop system-identification also requires the use of an appropriate system-identification algorithm to estimate the LSSM parameters from the IO dataset $\mathcal{D}^T$. The LSSM parameters 127 are estimated using subspace algorithms 126 based on the LSSM model structure 124 wherein Akaike's information criterion (AIC) may be used to select the optimal model order. While subspace methods have been extensively used in engineering and industry, the methods are disclosed here for the first time for identifying brain network IO dynamics. Designs of optimal input DBS waveforms for open-loop identification of brain network IO dynamics are disclosed in the following two sections.

BN-Modulated DBS Waveform in Open-Loop System-Identification.

Seemingly contradictory requirements for optimal input design, as pointed out above, make the input design problem challenging. The challenge may be overcome by separately designing a theoretically optimal input pattern and a clinically-safe DBS waveform. First, for the LSSM, $u_t$ is defined as the DBS parameters, hence the optimality for system-identification requires the input pattern $\{u_t\}^T_{t=1}$ to have an approximate white spectrum only in the DBS parameter domain. Second, clinical safety further requires the DBS waveform to be charge-balanced in short time intervals, therefore, the DBS waveform should consist of charge-balanced pulses. Third, while there are many input patterns that have white spectrum, they may not be easy to implement for DBS devices. Considering these three facts, we construct a novel DBS/stimulation waveform by choosing the input pattern (or equivalently, the DBS parameters) as binary noise (BN). As we describe in detail below, with this choice, our DBS waveform satisfies all constraints: (i) it is white in the DBS parameter space; (ii) it is clinically safe as it consists of change-balanced pulses; (iii) it is easy to implement as it only requires switching the DBS parameters between two values.

BN sequences may be used to design the input pattern. A BN sequence is a stochastic signal 200 that randomly switches between two fixed signal levels as shown in FIG. 2A. The BN sequence 200 has approximately white spectrum. A BN sequence is generated stochastically; at each time point $tT_{sw}$ (t=1, 2, 3, ... ), where $T_{sw}$ is the basic (fastest) switching time, the signal either remains at the previous level $L_1$ ($u_t = u_t-1 = L_1$) or changes to the other available level $L_2$ ($u_t = L_2 \neq u_t-1$) with equal probability, $$Pr(u_t = u_{t-1}) = 0.5; Pr(u_t \neq u_{t-1}) = 0.5. \quad (2)$$

The above BN sequence 200 has a spectrum that is white: its asymptotic discrete-time frequency spectrum $\Phi(\omega)$ is given by $$\Phi(\omega) = T_{sw}, \forall \omega \in 0, \frac{\pi}{T_{sw}}.$$

It should be noted that the frequency $\omega$ here means how frequently the DBS parameters are changing overtime, and should not be confused with the pulse frequency in the DBS waveform. $\omega = 0$ means the DBS parameters are constant over time. BN is generally regarded as an "optimal" test signal in the system-identification literature since it excites all frequencies $$\omega \in 0, \frac{\pi}{T_{sw}}$$

with approximately equal power.

To design the DBS waveform, independent BN sequences may be applied to each input dimension in $u_t$, i.e., to each DBS parameter. Thus, the DBS waveform is a pulse train consisting of pulses modulated by BN DBS parameters, termed as BN-modulated DBS waveform. As an example, consider a biphasic DBS pulse train 210 with two adjustable parameters, i.e., pulse frequency and amplitude, as shown in FIG. 2B. After choosing a proper $T_{sw}$, two independent BN sequences $BN_t^1$ and $BN_t^2$ are generated, with time-varying frequency $f_t$ (Hz) and amplitude $a_t$ (mA) set as $f_t = BN_t^1$, $a_t = BN_t^2$. Here, the two levels of BN represent a range of the time-varying DBS parameters. In this example of a biphasic pulse train 210, pulse frequency, $L_1 = 50$, $L_2 = 100$; and pulse amplitude, $L_1 = 3$, $L_2 = 6$ as diagrammed in FIG. 2B. Therefore, during the time interval $[t_0 T_{sw}, t_0 T_{sw} + T_{sw}]$, the BN-modulated DBS waveform consists of biphasic pulse trains with pulse frequency $BN_{t_0}^1$ and amplitude $BN_{t_0}^2$.

GBN-Modulated DBS Waveform and Identification Time.

A BN input pattern is theoretically optimal for system-identification assuming no constraint on the required identification time T in $\mathcal{D}^T$. However, there exist cases where the time available for stimulation to perform system-identification is limited. In this time-limited case, the performance of BN input pattern in system-identification will degrade, as explained below under the heading "GBN-Modulated DBS Waveform Reduced System-Identification Time." Hence improvement of the BN input pattern may be desirable for time-limited cases. Improvement may be achieved by incorporating the time-constant information of the underlying brain network dynamics to reduce T.

The idea is to utilize the concept of generalized binary noise (GBN). GBN is a direct generalization of BN, where $u_t$ stays at the same level with probability p rather than with fixed probability 0.5, i.e., $$Pr(u_t = u_{t-1}) = p; Pr(u_t \neq u_{t-1}) = 1 - p. \quad (3)$$

Compared with BN, which has a fixed p=0.5, GBN has an extra parameter p that can be tuned. Instead of the white spectrum of BN, a GBN with p>0.5 has more low frequency components and vice versa for p<0.5. An example of a GBN signal 220 with p=0.9 is diagrammed in FIG. 2C. Hence p can be tuned to achieve more accurate estimation of frequency ranges that are important in the brain network dynamics by putting more weight on these ranges. The time-constant $T_c$ of the brain network dynamics guides the choice of p as $$p = 1 - \frac{T_{sw}}{T_c}. \quad (4)$$

The fastest switching time $T_{sw}$ may be selected to be less than $T_c$, such that BN has white spectrum over frequency interval $$\omega \in \left[0, \frac{\pi}{T_{sw}}\right]$$

that covers the main frequency components $$\left[0, \frac{\pi}{T_c}\right]$$

of the brain network dynamics.

While it is possible to use the time-constant information to instead tune the basic switching period of the BN input pattern (e.g., a BN input pattern with $$T'_{sw} = \frac{T_c}{2},$$

which keeps p=0.5), for brain network dynamics with $T_c \gg T_{sw}$, this tuned BN input pattern has the disadvantage that its spectrum vanishes at $$\omega = \frac{2k\pi}{T_{sw}}, k = 1, 2, 3, \ldots$$

This introduces a considerable number (around $$\frac{T_c}{T_{sw}})$$

of undesirable "gaps" within the frequency band $$\left[0, \frac{\pi}{T_{sw}}\right].$$

Therefore this tuned BN does not have white spectrum across the entire band $$\left[0, \frac{\pi}{T_{sw}}\right];$$

it cannot excite the frequency components at these "gap frequencies", and can lead to a considerable loss of information. In contrast, GBN spectrum does not vanish at any point within $$\left[0, \frac{\pi}{T_{sw}}\right].$$

Hence under the condition that the identification time is the same, GBN input pattern can outperform BN input pattern in identifying linear dynamics as long as the time-constant information of the dynamics is available.

Therefore, to design the GBN input pattern, a rough estimate of the time-constant $T_c$ is needed. This estimate may be obtained by conducting an extra open-loop experiment where an on-off input pattern is applied, the rise time needed for each output feature to finish 36.79%, i.e., $$\frac{1}{e},$$

of the entire transition period is calculated, and these rise times across all output features are averaged to get the estimated time-constant $\hat{T}_c$. The duration of this extra stimulation is typically much shorter than the extra identification time BN needs, as explained in more detail below under the heading "GBN-Modulated DBS Waveform Reduced System-Identification Time."

Closed-Loop Simulation Testbed with Neuro Omega™.

Figure 3A:
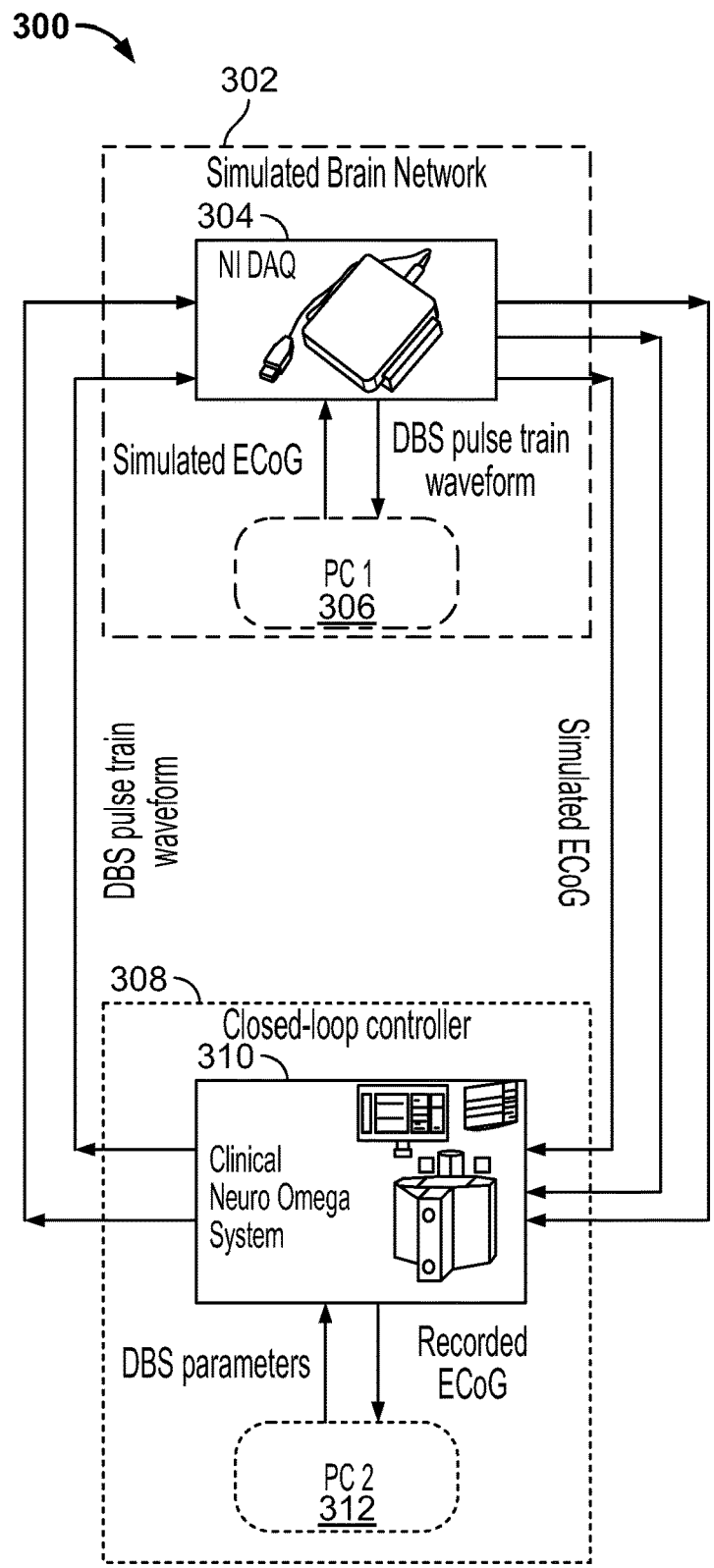
FIG. 3A is a block diagram illustrating components of a brain-simulation testbed.

A new real-time closed-loop simulation testbed 300 is needed to validate the brain network IO identification framework, for example as shown in FIG. 3A. A suitable testbed may be constructed using the clinical Neuro Omega™ microelectrode recording and stimulation system 310 (Alpha Omega Co. USA Inc., Alpharetta, Ga.), abbreviated as Neuro Omega™ for simplicity. This allows implementing the proposed open-loop system-identification framework in a clinical device, and testing the system-identification performance in simulated real-time closed-loop DBS control experiments.

As an overview, the simulation proceeds as follows. The Simulated Brain Network 304 generates a simulated ECoG which is sent to the closed-loop controller 308. The controller 308 includes the Neuro Omega™ 310, which records the simulated ECoG and sends it to the computer for the controller 312 (PC2). The controller 308 using PC2 312 determines a input pattern (i.e., DBS parameters) based on the feedback ECoG, and which the Neuro Omega™ 310 uses to generate pulse train DBS waveforms. The Neuro Omega™ 310 sends the DBS waveform to the Simulated Brain Network 304, which generates the simulated ECoG in response to the DBS waveform, thus closing the loop. A National Instrument Data Acquisition (NI DAQ) card may be used to implement digital-to-analog conversion (DAC) and analog-to-digital conversion (ADC). It should be appreciated that PC1 306 and PC2 312 although logically separate may share hardware components, and may consist of the same or different hardware components (e.g., hardware processor, computer memory, internal bus, etc.). As a concrete example, the closed-loop simulation testbed 300 was implemented for mood symptom control in depression, as explained below.

Simulated Brain Network.

FIG. 3B shows a process flow 320 for a simulated brain network 304 receiving DBS pulse train input from which DBS parameters are calculated or extracted 322 to obtain $u_t$. Brain network dynamics under depression may be simulated by a modified LSSM 324, as follows:

$$x_{t+1} = Ax_t + Bu_t + B\bar{d} + w_t$$

$$y_t = Cx_t + Du_t + D\bar{d} + v_t$$

$$s_t = Tx_t \quad (5)$$

The constant low level of mood characteristic of depression (i.e., a low mood) may be modeled by a time-invariant unknown disturbance $\bar{d}$. A mood symptom $s_t$ may be quantified by a linear combination of the hidden network state $x_t$ through matrix $T \in \mathbb{R}^{1 \times n}$. This mood symptom in depressed patients would take a negative value (e.g., $s_t = -40$, indicating "depressed") and the closed-loop controller should target a neutral mood symptom (i.e., $s_t = 0$). The variable $\bar{d}$ may be set as $\bar{d} = [T(I-A)^{-1}B]^\dagger \times s_{depression}$ such that when $u_t = 0$, the mean value of the steady-state neural mood symptom is $\bar{s} = s_{depression}$. To simulate a depressed patient, the value of $s_{depression}$ may be set $s_{depression} = -40$. Referring to FIG. 3B showing a simulated brain network 302 in a testbed 300, the modified LSSM is built as an example to simulate neural activity under depression. The LSSM 324 may be implemented in a personal computer (PC1) 306 (FIG. 3A). The input $u_t$ may be simulated as DBS pulse frequency and amplitude, and $y_t$ as ECoG powers or log-powers. The output $y_t$ is amplitude modulated 328 according to a dataset of ECoG waveform templates 326 in computer memory. More details are provided under the heading "Simulation Procedure" below.

Identification of T and $\bar{d}$.

To fully identify the depression LSSM 324, apart from estimating the LSSM parameters n, A, B, C, D, Q, R and S based on $\mathcal{D}^T = \{u_t, y_t\}_{t=1}^T$ using methods explained above, an extra open-loop dataset is needed to estimate T and $\bar{d}$. Using the simulation testbed, at rest (i.e., no stimulation $u_t=0$) dataset is collected wherein the patient's mood symptom $s_t$ is indicated and time-correlated to the ECoG, resulting in an extra open-loop dataset $$O^{T_0} = \{s_t, y_t\}_{t=1}^{T_0}.$$

Based on $y_t$, the hidden states $x_t$ of the simulated brain network are estimated by using a Kalman filter (see heading "Kalman Filter" below). First the mean of the measured $\{s_t\}_{t=1}^{T_0}$ is removed and the mean of the measured $\{y_t\}_{t=1}^{T_0}$ is removed. Then the neural state is estimated using the Kalman filter with $u_t$ and $\bar{d}$ set at 0. T is estimated from the mean-subtracted observed mood symptom $\{s_t\}_{t=1}^{T_0}$ and these Kalman-estimated states $$\{\hat{x}_{t|t}\}_{t=1}^{T_0}$$

by least squares regression. The data object $\hat{s}_t = T\hat{x}_{t|t}$ is defined as the neural signature for mood symptom. While the mood symptom is assumed to be known for this open-loop dataset (e.g., by behaviorally measuring it through self-reported questionnaires), in subsequent closed-loop control, the controller only observes ECoG and has no direct information of the true mood symptom $s_t$. Instead, the controller estimated the mood symptom by calculating the neural signature $\hat{s}_t$ based on the observed ECoG.

Finally, the controller estimates $\bar{d}$ from the mean mood symptom $$\bar{s} \approx \frac{1}{T_0} \sum \frac{T-1}{t=0} s_t$$

and the mean neural feature $$\bar{y} \approx \frac{1}{T_0} \sum \frac{T-1}{t=0} y_t$$

by solving a set of linear equations as described under the heading Identification Of Unknown Disturbance $\bar{d}$ below. Note that in practice, identification time T is typically constrained to be short but not $T_0$, because at-rest data can be obtained over a long time period.

Closed-Loop Controller Design.

Once the LSSM 324 is fully identified, a standard linear-quadratic-Gaussian (LQG) closed-loop controller 308 is designed to control the network activity. The LQG controller 308 includes a recursive Kalman state estimator and a linear-quadratic-regulator (LQR) feedback controller. Derivation of Kalman filter is straightforward and more detail presented below under the heading Kalman Filter. More briefly, the LQR controller design uses an LQR cost function defined as $$J(u_t) = \sum_{t=0}^{\infty} x_t^T T^T T x + (u_t - u^*)^T R_w (u_t - u^*).$$

Here u* is the steady-state DBS parameters required to maintain the target level s*=0, which can be computed as $u^* = \bar{d}$. The optimal solution of $u_t$ is given by a linear feedback of the state $u_t = -Gx_t + u^*$. The feedback gain G is given by the Riccati equation solution. A constraint of positivity of the control variables may be imposed by bounding this solution. $x_t$ is given by the Kalman state estimate.

Computational aspects of the closed-loop controller 308 may be implemented by a second personal computer 312 (PC2) or by any suitable hardware processor. Referring to FIG. 3C, operational aspects of a process 330 for generating DBS parameters $u_t$ is shown, which may be executed by the computer 312. The computer calculates ECoG features as feedback to determine the closed-loop DBS amplitude and frequency (DBS parameters $u_t$) by the above LQG feedback control law. Both the LSSM and the closed-loop controller may run at a common time-step, e.g., 1 s.

In practical DBS scenarios, recorded neural signals are contaminated by stimulation artifacts. Typically, stimulation artifacts have larger amplitudes than neural signals, leading to low signal to noise ratio. Hence, the hardware processor removes stimulation artifacts 332 from the recorded ECoG in real time before calculating neural features $y_t$ 334 from the raw recorded ECoG. Although FIG. 3C indicates "power features" at block 334, it should be appreciated that any useful signal feature may be used. In the simulation testbed 300, stimulation artifacts may be simulated by referencing the generated ECoG to an amplified version of the input DBS pulse train waveform, such that the actual recorded signal is a superposition of ECoG and the large stimulation pulse train artifacts. Closed-loop control requires real-time removal of the stimulation artifacts, hence the process 330 includes execution of a real-time template-subtraction artifact removal algorithm 332 before neural feature calculation 334.

Figure 3D:
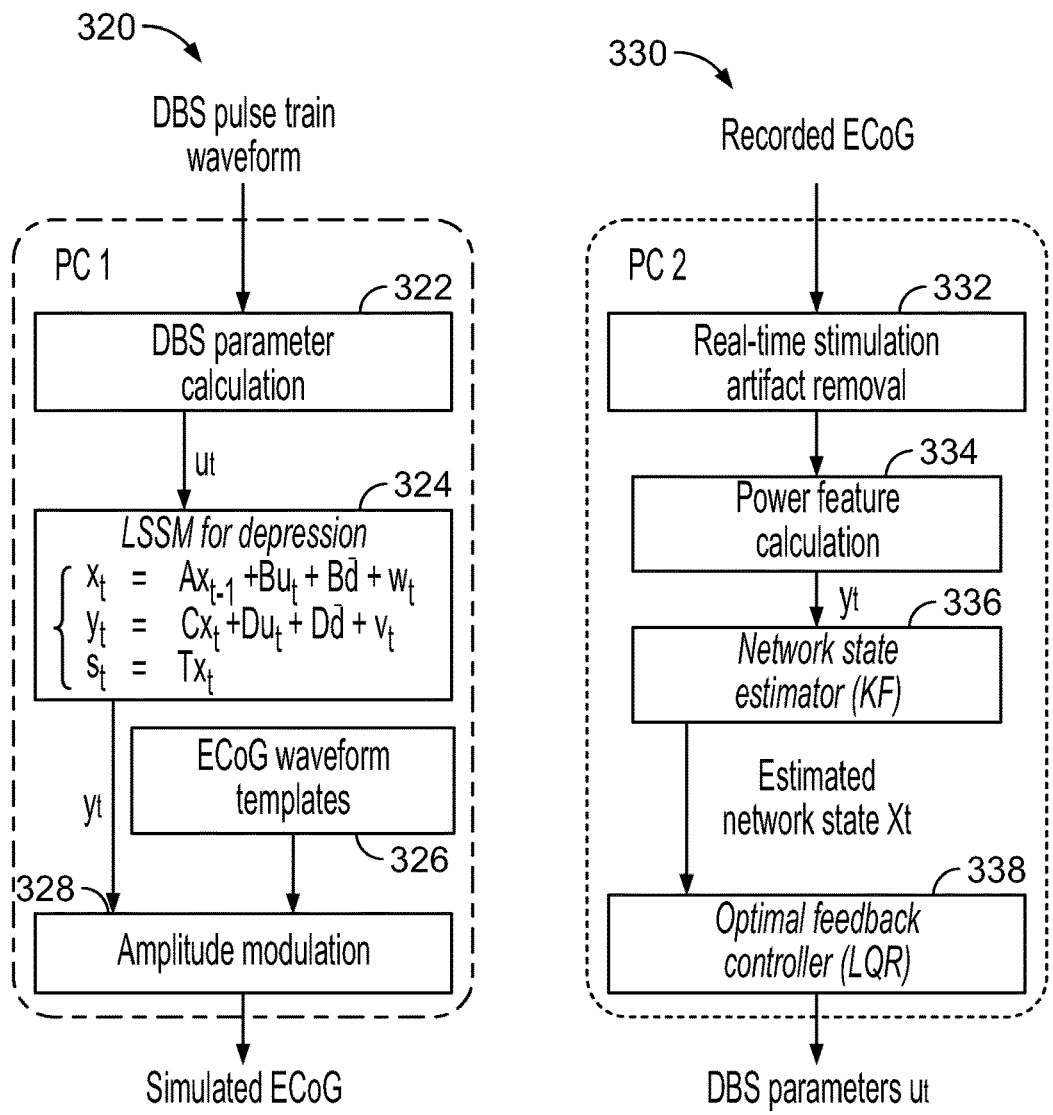
FIG. 3D is a flow diagram illustrating an overview of a design process for a closed-loop controller.
Figure 3D:
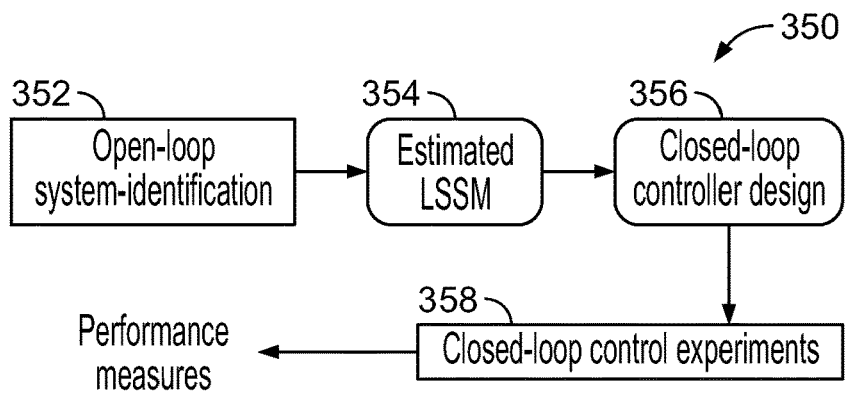

In summary of the foregoing, FIG. 3D illustrates higher-level aspects of a process 350 for design of a clinical closed-loop control process. Details may be as explained elsewhere herein. Open-loop testing is first performed for system identification at 352. From system identification 352, an LSSM for the system at hand is estimated 354. Note that in clinical settings, the LSSM will be estimated for each subject, although similar LSSMs may be identified for different subjects. In addition, system identification may need to be repeated for different closed loop control sessions with the same subject, because system parameters may drift over time or in response to variations in measurement, due to stimulation-induced changes or plasticity, or due to stimulation electrode networks (e.g., different equipment in the signal train). After system identification, the closed-loop controller is designed 356 based on the estimated system parameters (i.e., the estimated LSSM). At 358, the closed loop controller is tested experimentally 358 in a clinical setting, resulting in performance measures for the experiment. The performance measures indicate effectiveness of the closed loop controller in mitigating an undesired mood or mental condition (e.g., depression, anxiety, agitation) or enhancing a desired mood or mental condition (e.g., confidence, focus) based on cognitive feedback from the subject assessing the target mental state during the experiment. In an alternative, the closed-loop controller may be developed and tested using a simulation procedure as described below.

Simulation Procedures.

Multiple simulations may be run to test 350 a proposed IO identification framework by evaluating both open-loop identification 352 and closed-loop control 356 performances with subsequent control experiments 358, also consistent with FIG. 3D. Monte-Carlo simulations may be performed within computer programs. In addition, or in an alternative, real-time closed-loop control simulations may be implemented using the closed-loop simulation testbed 300 with Neuro Omega™.

Monte-Carlo Simulations.

The proposed IO identification framework may be tested using numerical simulations by a custom or commercial analysis computer program, e.g., Matlab™. An advantage of Monte-Carlo experiments is that the experiments can be completed in a short amount of time. The IO identification framework may be tested with BN input pattern 402 (FIG. 4A), where each DBS parameter is an independent BN sequence that satisfies equation (2), for example with $T_{sw}=1$ s, DBS amplitude levels $L_1=2$ mA and $L_2=6$ mA, and DBS frequency levels $L1=50$ Hz and $L2=100$ Hz. The upper solid line 401 represents the power spectral density of the BN input pattern, which is white across the frequency band. Three alternative input patterns are compared with the BN input pattern:

(i) rectangular pattern; each parameter has a rectangular shape: $u_t=L$, $\forall t \in [\frac{1}{4}T, \frac{3}{4}T]$ and $\beta_t=0$, $\forall t \in [0, \frac{1}{4}T] \cup [\frac{3}{4}T, \frac{1}{2}T]$, where $$L = \frac{L_1 + L_2}{2}.$$

Here the effective stimulation time is still T, but we set aside $$\frac{T}{4}$$

before stimulation and after stimulation to include the transition periods.

(ii) single-sinusoid pattern; each parameter has a sinusoid shape with a single frequency f chosen at random: $u_t=L+L \sin(2\pi ft)$.

(iii) multiple-sinusoid pattern; each input parameter is a superposition of six sinusoids:

$$u_t = L + \frac{L}{5} \sum_{k=1}^{6} \frac{6}{} \sin(2\pi f_k t),$$

with the frequencies $f_k$'s chosen at random.

For a sample Simulated Brain Network, random LSSM parameters may be generated as follows. First determine the model dimensions. For example, model order may be randomly selected n from $\{2, 3, \ldots, 20\}$, the number of stimulation input channels $m_1$ from $\{1, 2, \ldots, 10\}$, and the number of recorded output ECoG channels from $\{m_1, m_1+1, \ldots, 3m_1\}$ since in practice there are more output channels than stimulation channels. Then, the A, B, C, and D matrices may be randomly generated, for example, by the Matlab™ built-in function drss such that A is stable (eigenvalues inside the unit disk). Next, the noise covariance matrix is defined as a random positive-semidefinite matrix $\varepsilon \times U^T U$, where $U$ is a full-rank $(n+k) \times (n+k)$ random Gaussian matrix with unit variance, and $\varepsilon$ is randomly selected from [0.001, 0.05]. Finally, T may be set as random Gaussian matrix, and $\bar{d}$ may be set as $\bar{d}=[T(I-A)^{-1} B]^\dagger \times s_{depression}$, with $s_{depression}=-40$.

In open-loop identification experiments, an LSSM may be identified for each of the input patterns, wherein $T=120$ mins in $\mathcal{D}^T$ and $T_0=10$ mins in $\mathcal{O}^{T_0}$. The identified LSSMs may then be used design closed-loop controllers, referred to herein as a BN controller, rect controller, single-sin controller and multi-sin controller. A target objective is defined, for example, for the depression example the closed-loop controller may target a neutral mood $s^*=0$. Lower- and upper-bound limits on the DBS frequency may be defined, for example 0 to 150 Hz, and for the DBS current amplitude 0 to 8 mA.

As the comparison with "worst case" baseline in system-identification, stable LSSMs can be generated using the same method as in the Simulated Brain Network. These LSSMs may be referenced herein as "rnd" (random), and used to estimate the chance level system-identification error. As the comparison with "best case" baseline in closed-loop control, an oracle controller derived from the true LSSM used in Simulated Brain Network may be used. The oracle controller has the best possible closed-loop control performance.

Both system-identification and closed-loop control can be tested by running Monte-Carlo experiments across a large number (e.g., 100) of Simulated Brain Networks. In addition, for each of the Simulated Brain Networks, multiple system-identification and closed-loop control trials (e.g., ten each) may be performed with independent noises. Different controllers may be tested for comparative purposes. For example, for a particular Simulated Brain Network, Wilcoxon rank-sum tests may be run across the multiple closed-loop control trials. The performance of these multiple trials may be averaged as the final control performance of a given controller for this Simulated Brain Network. Wilcoxon signed-rank tests may similarly be performed to compare performance across the 100 Simulated Brain Networks.

Closed-Loop Simulations with Neuro Omega™.

In addition, real-time closed-loop simulations can be performed using the simulation testbed with Neuro Omega™. For example:

(i) To show the performance of BN-modulated DBS waveform when identification time is not constrained, a long identification time may be selected, i.e., $T=120$ mins. First, an ideal case where there exist no stimulation artifacts is simulated. The simulated controller in this case may be referred to herein as the "BN" controller.

(ii) Next stimulation artifacts and implement artifact removal algorithm may be added in both open-loop identification and closed-loop control. The simulated controller with this modification may be referred to herein as the "BN-with-artifact" controller.

(iii) To compare the performance of BN-modulated DBS waveform and GBN-modulated DBS waveform when identification time is restricted, two more input patterns may be tested. The first one is a shorter BN input pattern with T=20 mins. The resulting controller may be referred to herein as the "BN-20 mins" controller. The second input pattern may be a GBN input pattern with T=20 mins and $$p = 1 - \frac{T_{sw}}{\hat{T}_c}.$$

The resulting controller may be referred to herein as the "GBN-20 mins" controller. In this comparison, we also simulate the stimulation artifacts.

$T_{sw}$ may be set to 1 s in both BN input pattern and GBN input pattern, and the parameter levels the same as described above for the Monte Carlo simulation. For simplicity, for the Simulated Brain Network, a single stimulation channel may be simulated with a choice of the effective DBS parameters $u_t$ as the pulse frequency and amplitude. Therefore, the LSSM input dimension m=2=1 stimulation channel×2 DBS parameters. The output neural features $y_t$ may be selected as the ECoG powers or log-powers of plural frequency bands, for example, 1-4 Hz, 5-8 Hz, 9-16 Hz, 17-32 Hz, and 33-64 Hz. Two channels of ECoG may be simulated. Hence, in this example the LSSM output dimension k=10=2 ECoG channels×5 power features.

In total, two Simulated Brain Networks were tested by the authors hereof with independently generated random LSSMs. The first Simulated Brain Network (Simulated Brain Network 1) had a random underlying LSSM of order 3, with poles at 0.97, 0.95 and 0.93, and noise level ε=0.005. The second Simulated Brain Network (Simulated Brain Network 2) had a random underlying LSSM of order of order 4, with poles at 0.95, 0.90, 0.85 and 0.75, and a higher noise level ε=0.02. The closed-loop control design settings were the same as the previous section. For each of the Simulated Brain Network and each of the above four controllers, i.e., BN controller, BN-with-artifact controller, BN-20 mins controller and GBN-20 mins controller, the authors ran 10 trials of closed-loop control experiments and conducted Wilcoxon rank-sum tests to compare performance across the 10 trials.

Performance Measures.

The brain network IO identification framework may be evaluated both in open-loop identification experiments and in closed-loop control experiments. In open-loop identification, the relative estimation error of the IO dynamics can be quantified as $$E_{IO} \frac{\|\mathcal{G} - \hat{\mathcal{G}}\|_2}{\|\mathcal{G}\|_2}, \quad (6)$$

where $\mathcal{G}$ denotes the true LSSM and $\hat{\mathcal{G}}$ denotes the estimated LSSM. The norm $\|\cdot\|_2$ is the $\mathcal{H}_2$ norm of a dynamical linear system (see heading Definition of System Norm below). Similarly, the relative estimation error of the noise covariance can be quantified as $$E_{noise} \frac{\|\mathcal{N} - \hat{\mathcal{N}}\|_2}{\|\mathcal{N}\|_2}, \quad (7)$$

where $\mathcal{N}$ represents a dynamical system describing the IO dynamics from the noise terms $w_t$ and $v_t$ to the output $y_t$ in (1). $\mathcal{N}$ is termed noise dynamics, and is closely related to the noise covariance (Definition of System Norm). $\hat{\mathcal{N}}$ denotes the estimated noise dynamics.

In closed-loop control experiments, various metrics may be used. Steady-state performance may be evaluated by computing error $e_t$ between a controlled underlying mood symptom $s_t$ and a target level s*=0, i.e., $e_t=s_t$. The steady-state bias BIAS may be defined as $$\text{BIAS} = \text{mean}(e_t), \quad (8)$$

and the steady-state standard deviation STD as $$\text{STD} = \text{std}(e_t), \quad (9)$$

The mean and standard derivation may be calculated across data points at steady state. Transition time TranT may be defined as the time it takes to complete 95% of the transition from the steady state before closed-loop control to the steady state with closed-loop control. Estimation performance error EstE of the estimated neural signature $\hat{s}_t$ with respect to the true mood symptom $s_t$ may be calculated as $$EstE = \frac{\sqrt{\sum_{t=0}^{N-1}(s_t - \hat{s}_t)^2}}{\sqrt{\sum_{t=0}^{N-1} s_t^2}} \quad (10)$$

where $\hat{s}_t = T\hat{x}_{t|t}$ is the estimated neural signature with $\hat{x}_{t|t}$ given by the Kalman filter and N is the total closed-loop control experiment time.

Results: BN Input Pattern Achieved Accurate Open-Loop Model Identification: Monte Carlo Simulations.

Figure 4A:
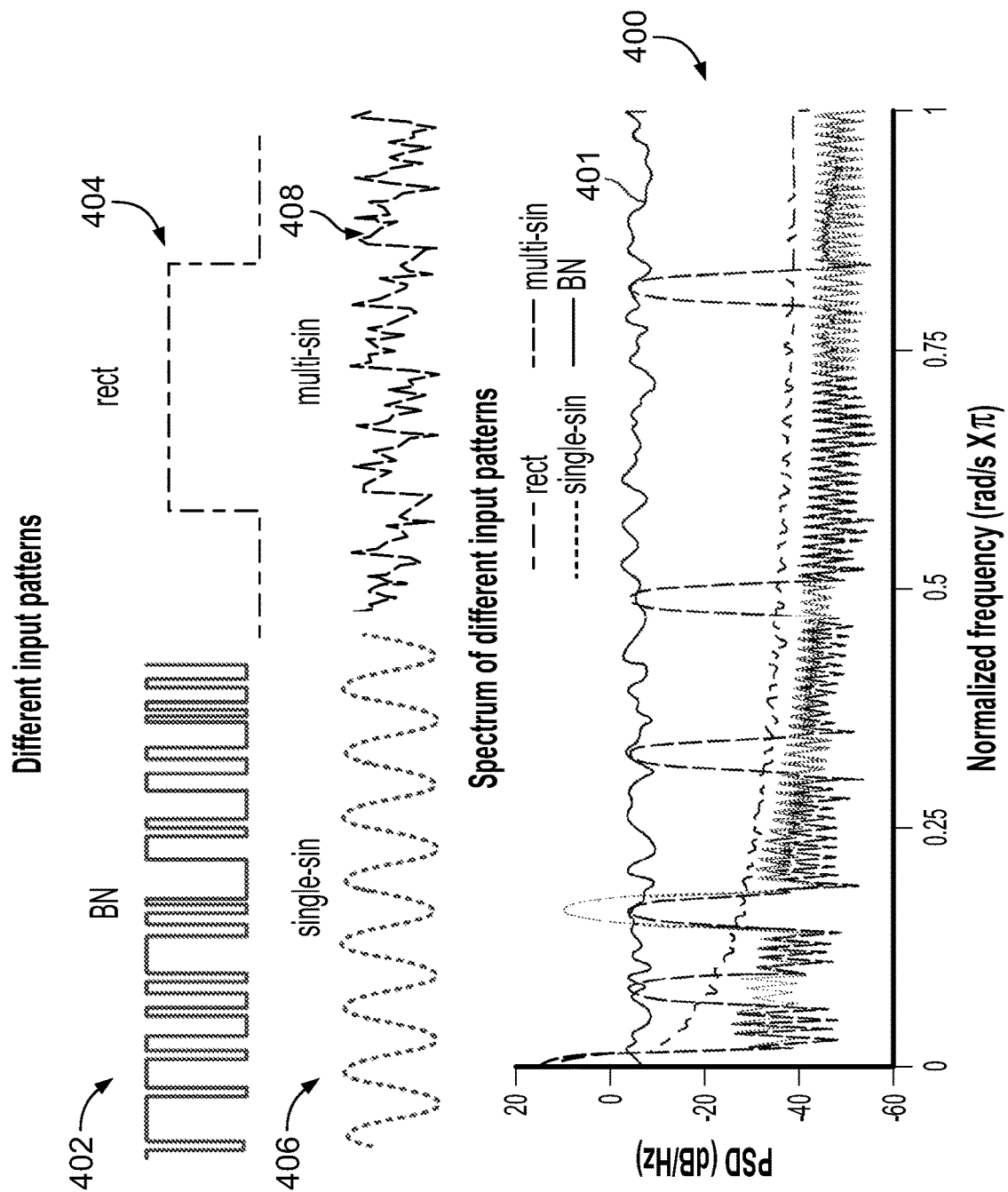
FIG. 4A is a power spectral density (PSD) graph illustrating PSD for four different types of input patterns.
Figure 4B:
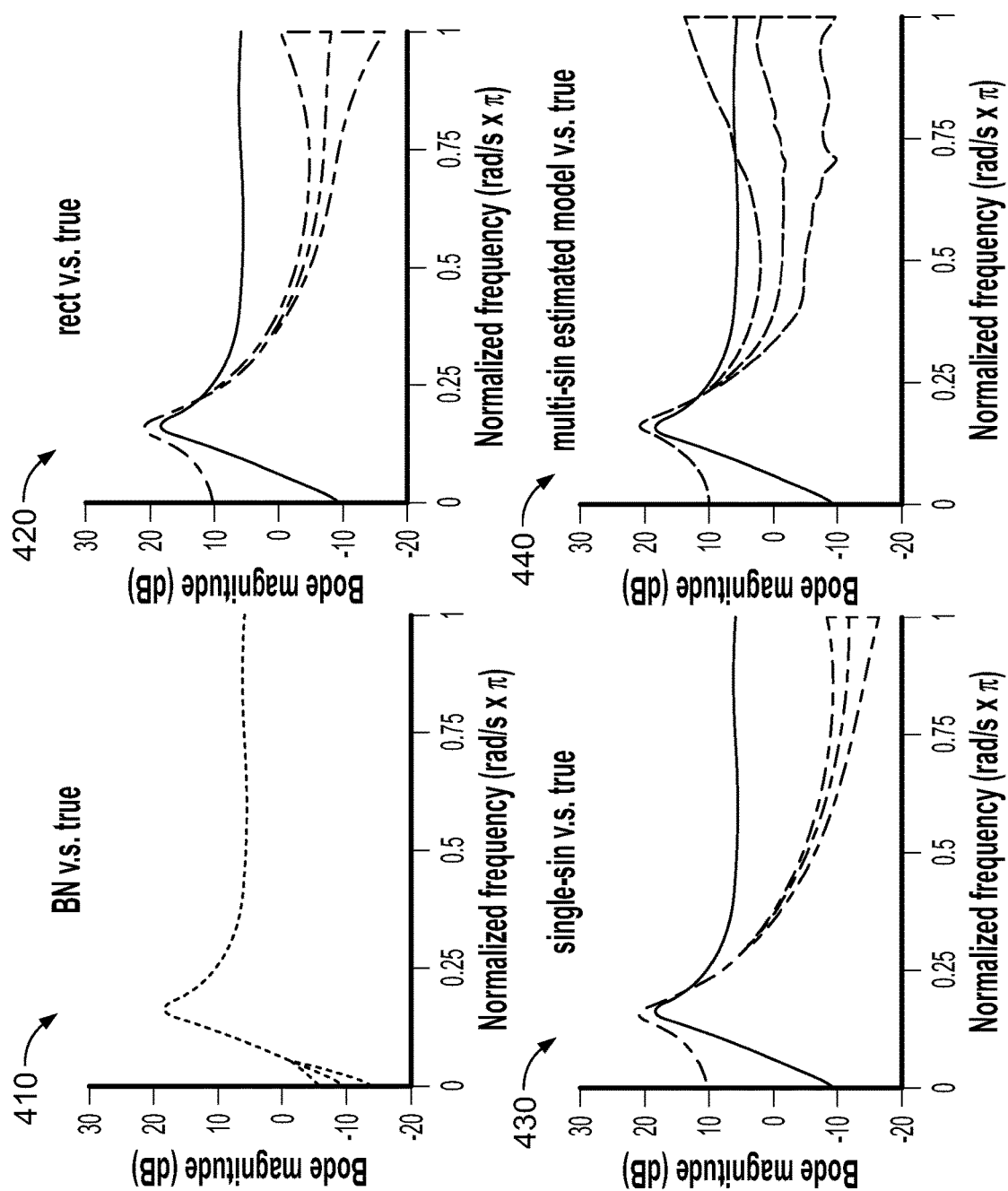
FIG. 4B shows four related Bode plots each for a different input pattern.

Monte Carlo system-identification simulations were performed to compare the four input patterns described in connection with FIG. 4A above. Power spectrums of each input pattern were estimated by Welch's method, and show that the BN input pattern has approximately white spectrum. The spectrums of other input patterns are concentrated around particular frequencies. To see an example of how the input patterns affected identification results, a sample Simulated Brain Network was generated and four LSSMs using the four input patterns were identified. The estimated IO transfer functions from the 1st input channel to the 1st output channel for a BN input pattern is shown as the Bode plot 410 in FIG. 4B. Similarly, the Bode plot 420 compares transfer functions for a rectangular input pattern, Bode plot 430 for a single-sine input pattern, and Bode plot 440 for a multi-sine input pattern. Compared with other input patterns, the BN input pattern led to a more accurate estimate of the underlying IO dynamics with less bias and variance.

Figure 4C:
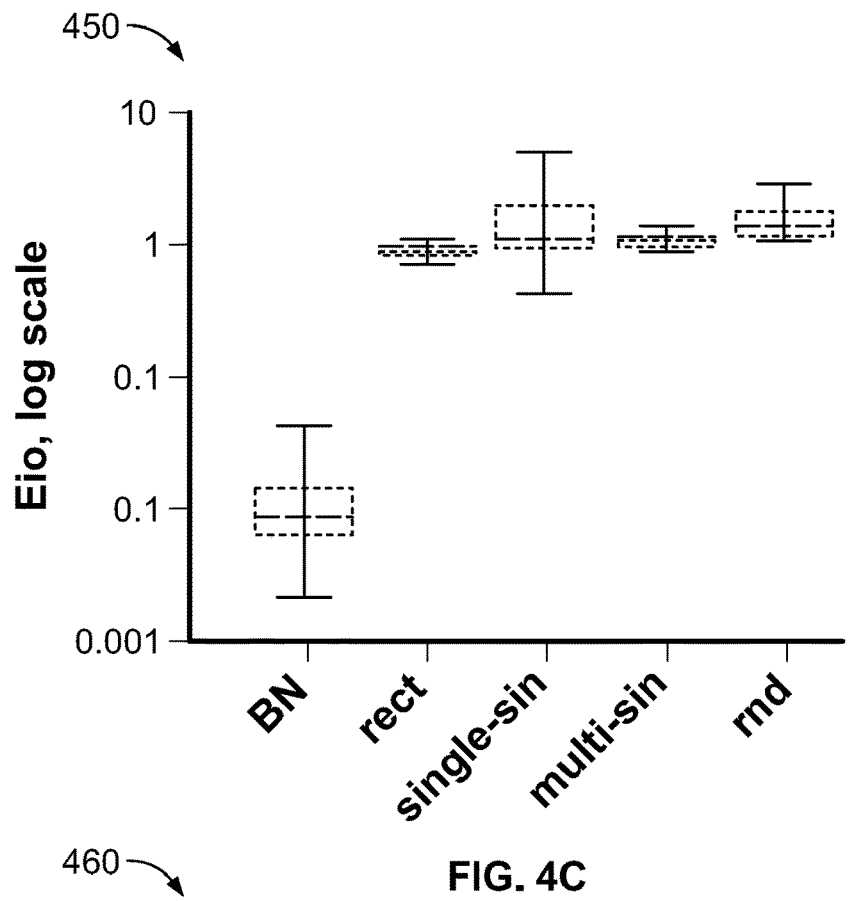
FIG. 4C shows boxplots comparing IO dynamics estimation error for different input patterns.
Figure 4D:
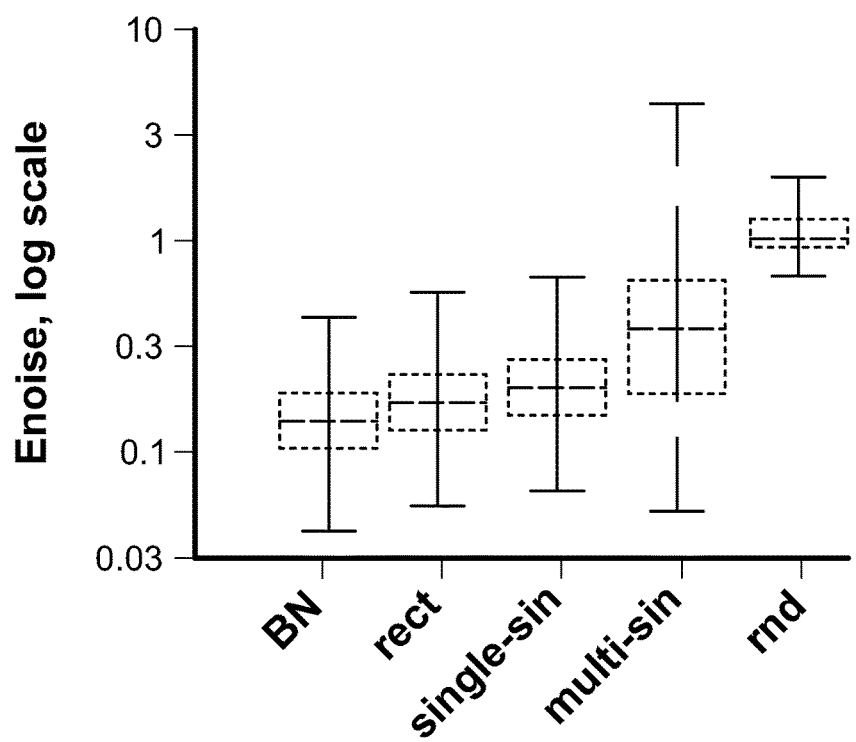
FIG. 4D shows boxplots of the noise dynamics estimation errors for different input patterns across 100 random underlying LSSMs.

The above observations in Monte-Carlo simulations were quantified. 10 estimation error of the BN input pattern was much smaller than other input patterns as shown in the boxplots 450 of FIG. 4C (median $E_{IO}$, BN: 0:0094; rect: 0:9210; single-sin 1:0831; multisin 0:9451; rnd 1:4114). In FIG. 4C, The lower and upper bound of the boxes represent the 25th and 75th percentiles of the absolute error distribution and the middle line in each box represents the median. Whiskers represent the 95th and 5th percentile of the absolute error distribution. The same holds for all subsequent box plots. In estimating the IO dynamics, BN is advantageous because it has white spectrum and can excite the entire frequency band with equal energy and without bias towards specific bands. The BN input pattern also estimated the noise dynamics successfully, with much smaller error than the chance level performance as shown in the boxplots 460 of FIG. 4D (median $E_{noise}$, BN: 0:1692 v.s. rnd: 1:0742). The four input patterns had comparable estimation errors of the noise dynamics, because noise dynamics were driven by $w_t$ and $y_t$, which were independent of the input patterns $u_t$.

Figure 5A:
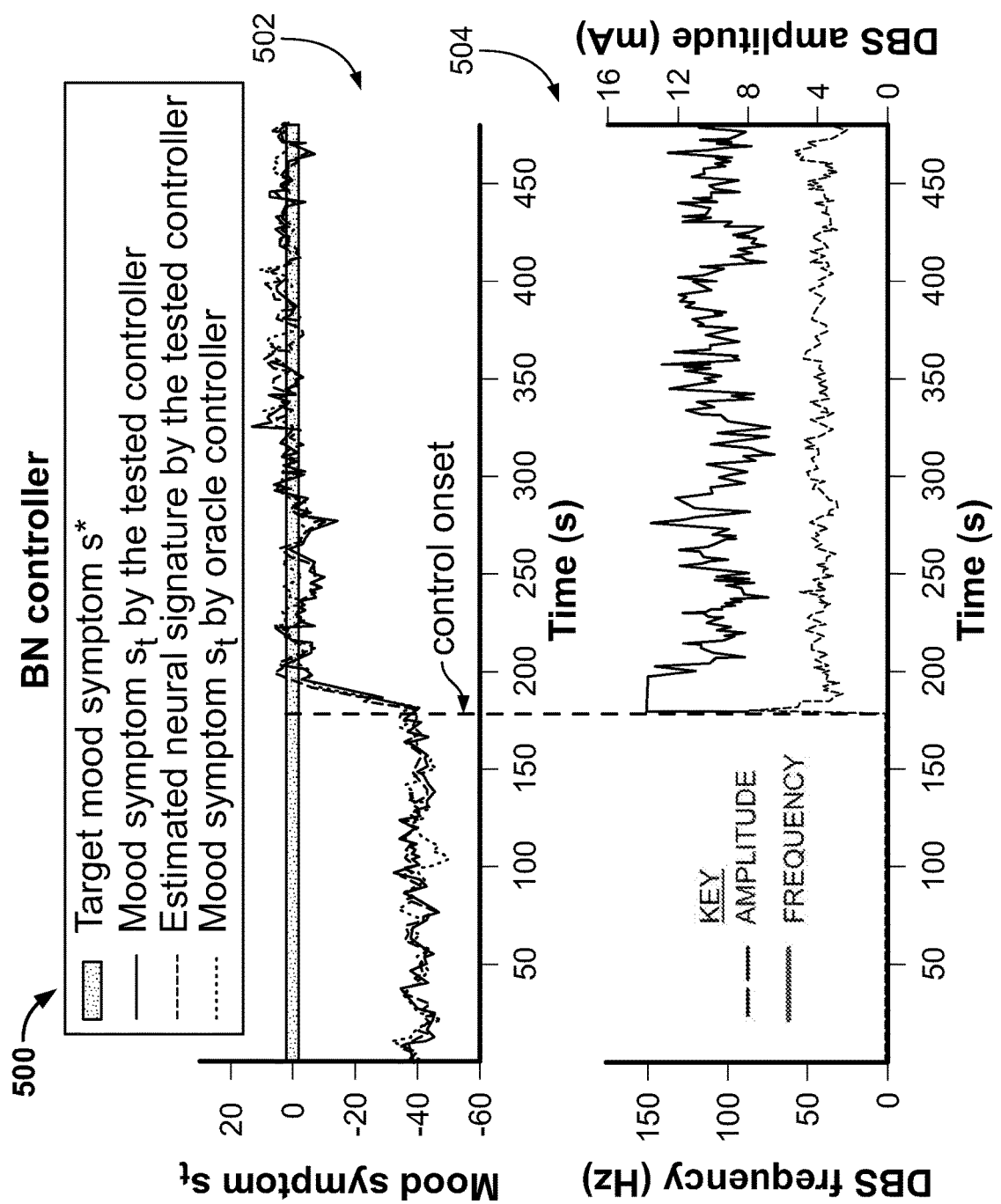
FIG. 5A shows a chart of a binary noise (BN) controller in a closed-loop Monte Carlo simulation.
Figure 5B:
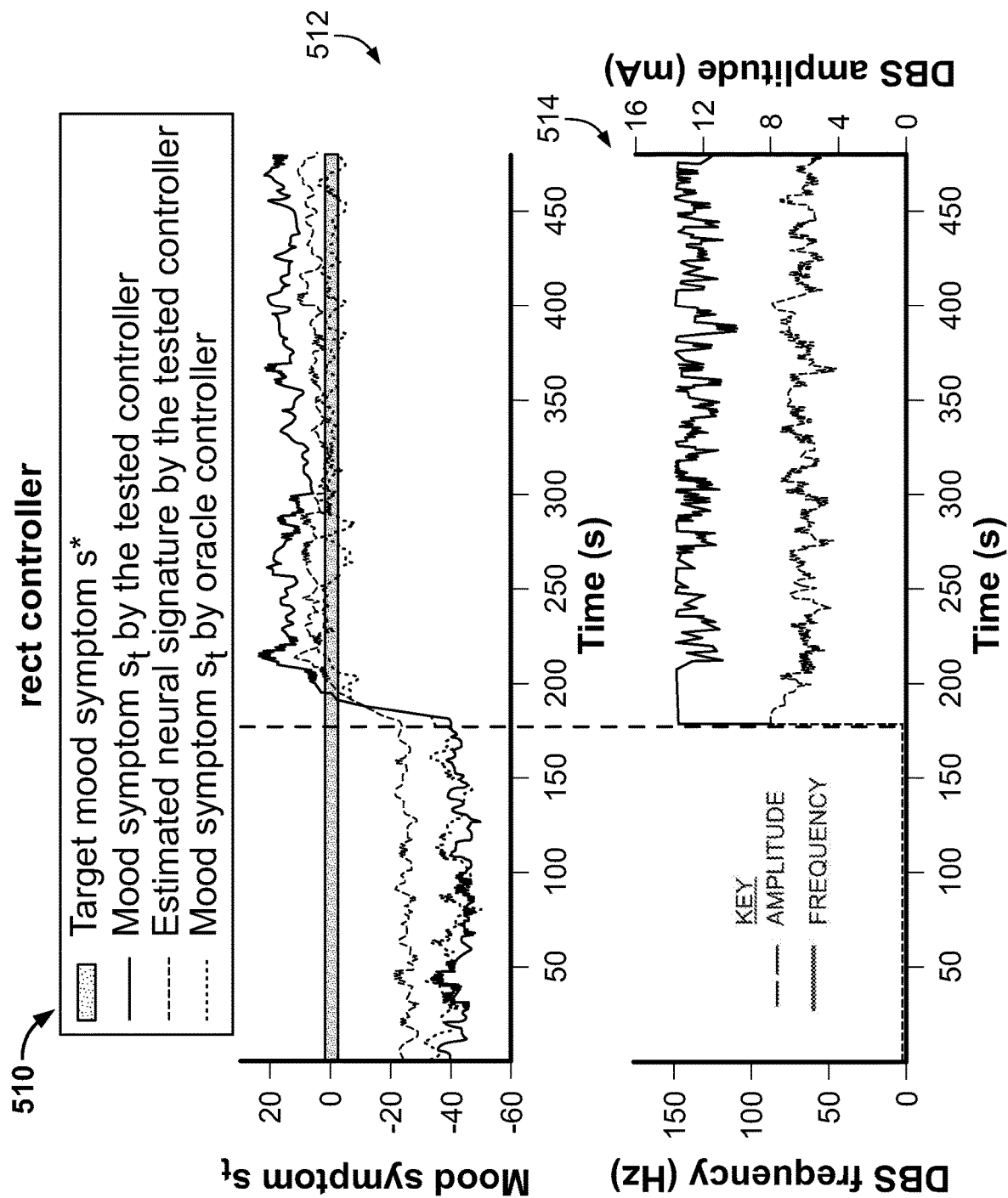
FIG. 5B shows a chart of a rectangular (rect) controller in a closed-loop Monte Carlo simulation.
Figure 5C:
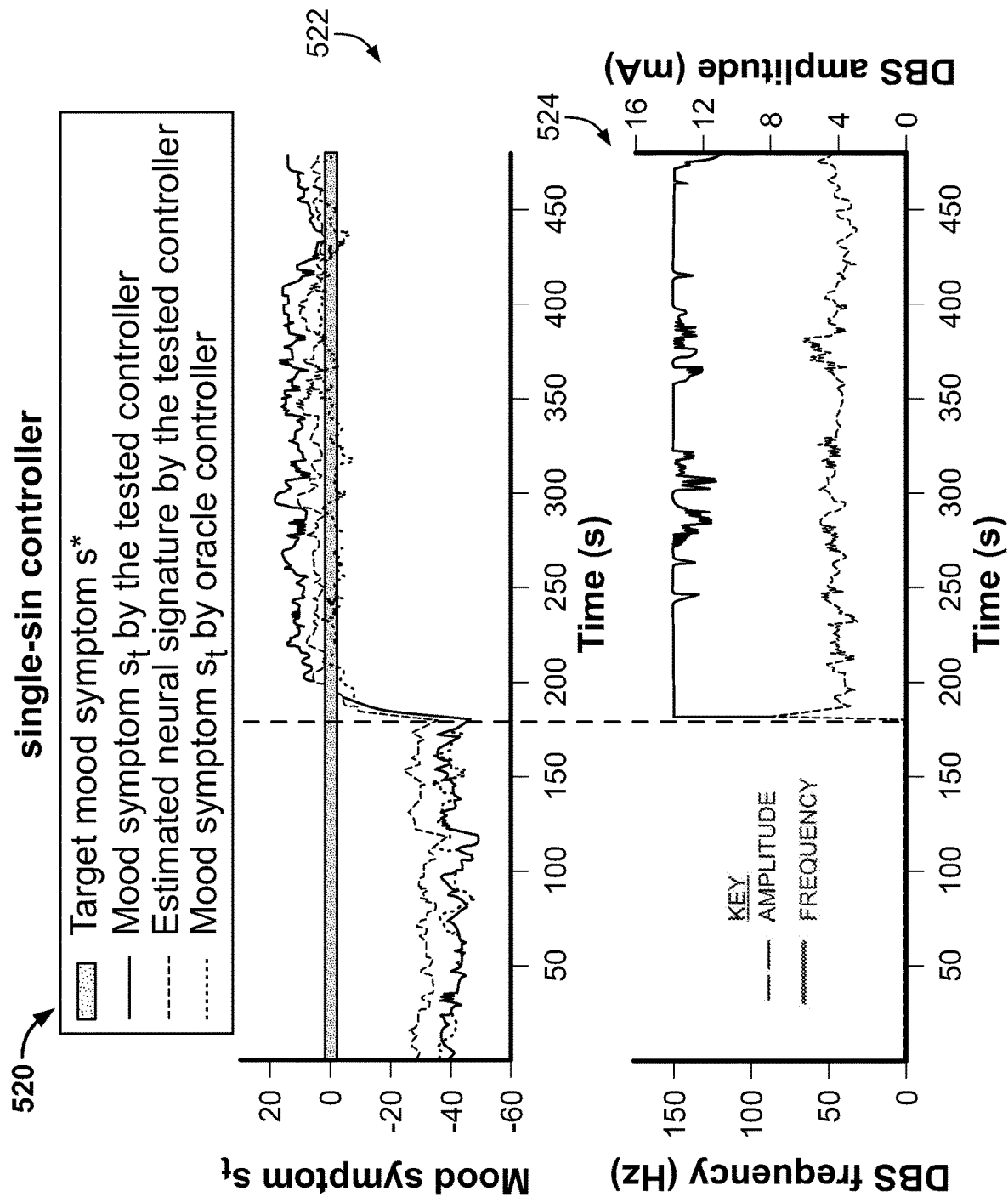
FIG. 5C shows a chart of a single-sine controller in a closed-loop Monte Carlo simulation.
Figure 5D:
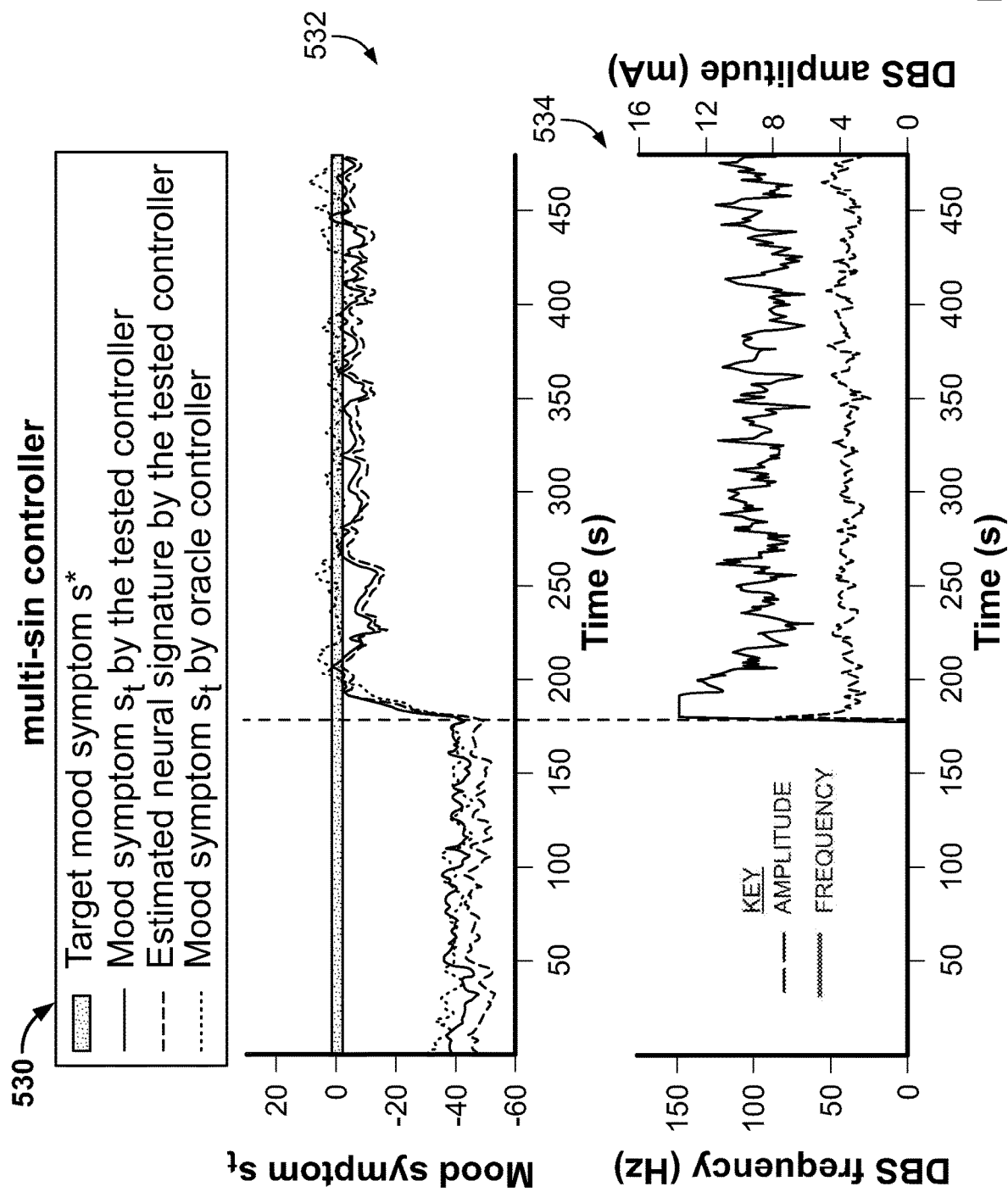
FIG. 5D shows a chart of a multi-sine controller in a closed-loop Monte Carlo simulation.
Figures 5E, 5F:
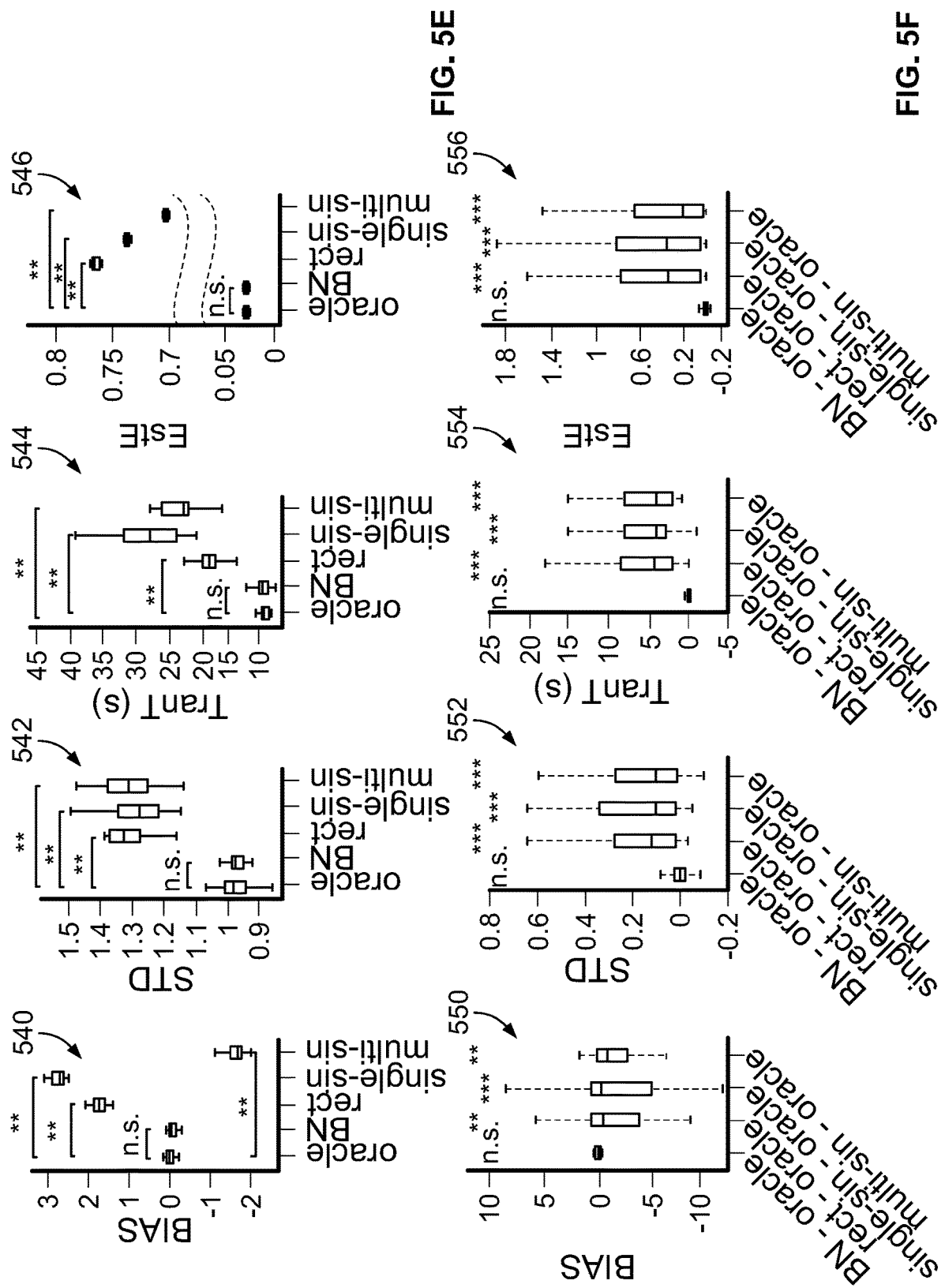
FIG. 5E shows controller comparisons for a sample Simulated Brain Network across 10 trials.
FIG. 5F shows controller comparisons in Monte-Carlo experiments over 100 Simulated Brain Networks.

Results: BN Controller Achieved Precise Closed-Loop Control of Mood Symptom:

Monte Carlo simulations. The brain IO dynamic identification framework was further validated by evaluating how the identified models influenced closed-loop DBS control. FIGS. 5A-D show results of a control session for a sample Simulated Brain Network. The BN controller 500 controlled the mood symptom $\hat{s}_t$ to follow the target closely, as shown in the symptom target graph 502 and DBS frequency graph 504 in FIG. 5A (BIAS=−0.05 and STD=0.98) by actively changing the DBS frequency and amplitude according to neural feedback. The estimated neural signature $\hat{s}_t$ closely followed the mood symptom as shown in FIG. 5A (EstE=0.03). In addition, the BN controller performed similar to the best case oracle controller as also shown at FIG. 5A, 502. Closed-loop control performance of the BN controller (i.e., BIAS 540, STD 542, TranT 544 and EstE 546, see above) as shown in FIG. 5E was not significantly different from the oracle controller across the 10 closed-loop control trials with independent noises (BN v.s. oracle; Wilcoxon rank-sum tests, P>0.15 for all performance measures).

In contrast, the other three controllers had a large bias in controlling the mood symptom $s_t$ at steady state. Charts 512, 514 of FIG. 5B show a large bias for a rectangular input controller 510, compared to target and to oracle. Charts 522, 524 of FIG. 5C show a similar bias for a single sine controller 520. For the multi-sine controller 530, a similar bias appears in charts 532, 534 of FIG. 5D. Also, FIGS. 5B-D show the estimated neural signatures $\hat{s}_t$ were biased from the underlying mood symptom $s_t$. Compared with the oracle controller, the performance of these three controllers was significantly worse, as shown in FIG. 5E (rect v.s. oracle, single-sin v.s. oracle, multi-sin v.s. oracle: P<0.05 for all performance measures).

We further conducted Monte Carlo simulations in which we controlled 100 independent Simulated Brain Networks, the results of which are depicted in FIG. 5F, wherein chart 550 show BIAS, chart 552 shows STD, chart 554 shows TranT, and chart 556 shows EstE. The performance of the BN controller and the oracle controller was not significantly different across the 100 Simulated Brain Networks for BN v.s. oracle (Wilcoxon signed-rank tests, P>0.35 for all performance measures). For the other three controllers, the performance was significantly worse than the oracle controller (Wilcoxon signed-rank tests, P<0.05 for all performance measures).

Combined, the results demonstrate that i) input pattern in open-loop system-identification has critical influence on subsequent closed-loop control performance, and ii) that the novel BN input pattern can achieve accurate IO dynamics identification and thus, enable accurate closed-loop control of the mood symptom.

Results: BN Controller Achieved Accurate Closed-Loop Control of Mood Symptom: Neuro Omega™ Simulations.

Figure 6A:
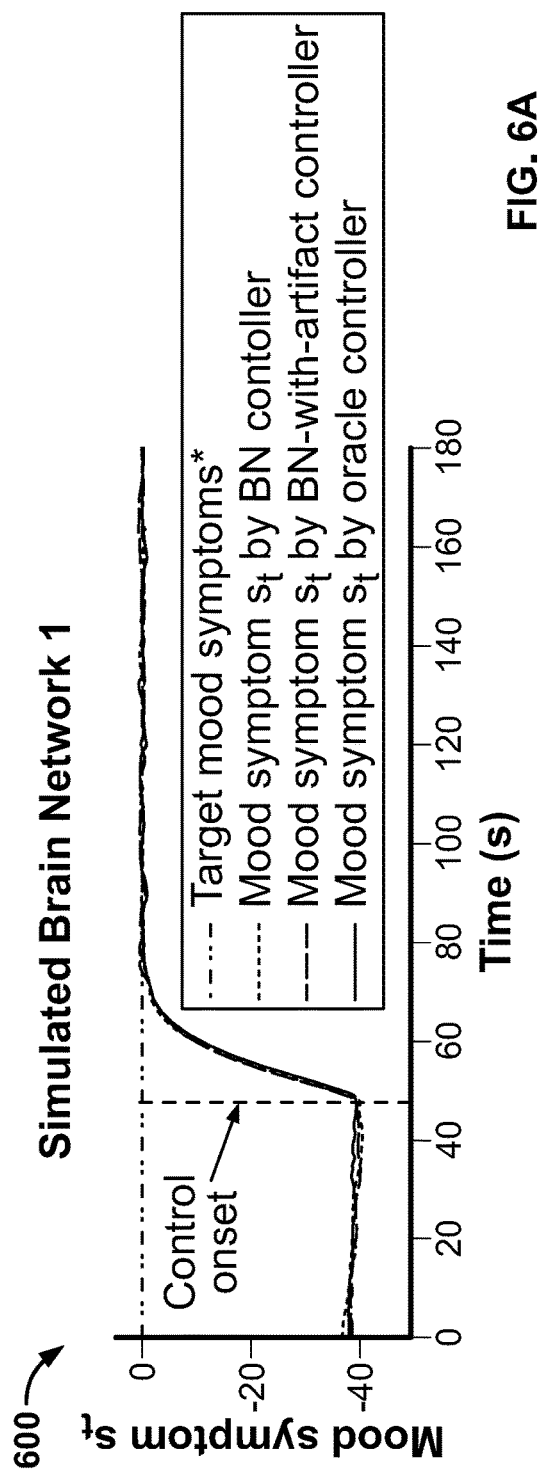
FIG. 6A is a chart comparing BN controllers with an oracle controller and target in a Neuro Omega™ simulation, for a first brain network.

Simulations using the closed-loop simulation testbed with Neuro Omega™ were also conducted. For both Simulated Brain Network 1 and Simulated Brain Network 2, the controlled mood symptom using BN controller followed the target tightly at steady-state and was close to the oracle controller as shown in chart 500, FIG. 6A (Brain Network 1) and chart 620, FIG. 6B (Brain Network 2). The performance of BN controller and oracle controller was not significantly different for both brain networks across the 10 closed-loop simulation trials as shown in the boxplots 610, 612, 614, 616 of FIG. 6B (Simulated Brain Network 1, BN v.s. oracle, Wilcoxon rank-sum tests, P>0.4 for all performance measures; and boxplots 630, 632, 634, 636 of FIG. 6D (Simulated Brain Network 2, BN v.s. oracle; Wilcoxon rank-sum tests, P>0.5 for all performance measures).

Results: BN Controller Achieved Accurate Performance in Face of Stimulation Artifacts: Neuro Omega™ Simulations.

Figure 6B:
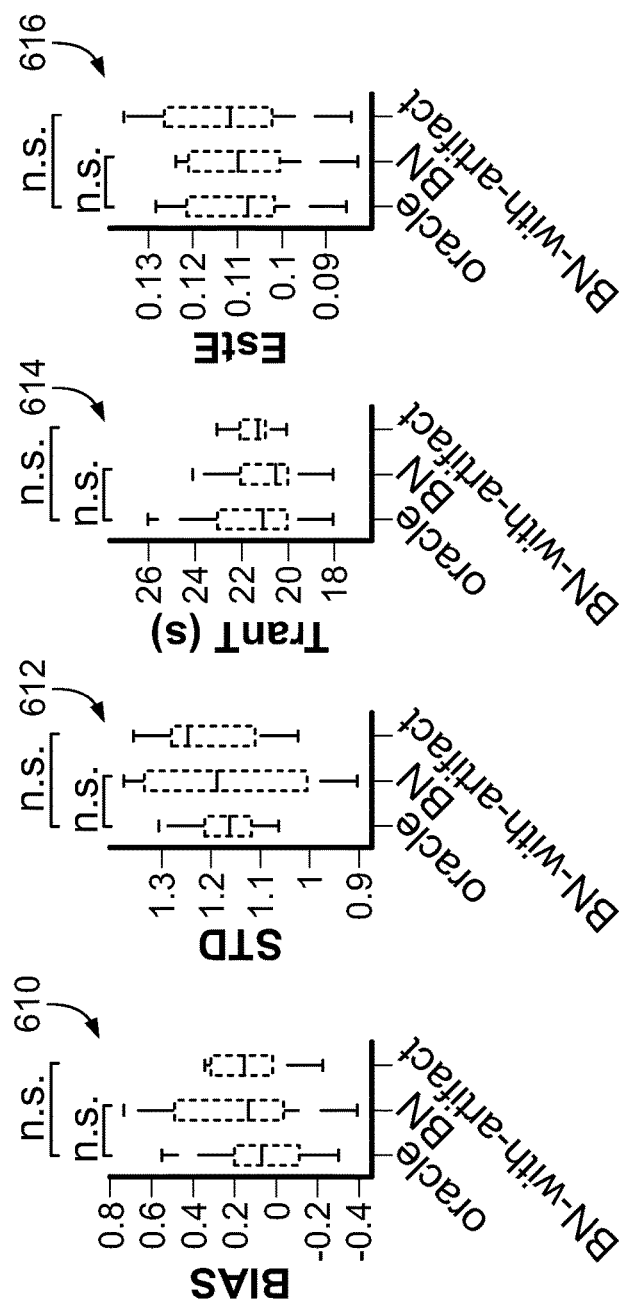
FIG. 6B shows boxplots comparing results for different measures across 10 trials of the comparison represented by FIG. 6A.
Figure 6C:
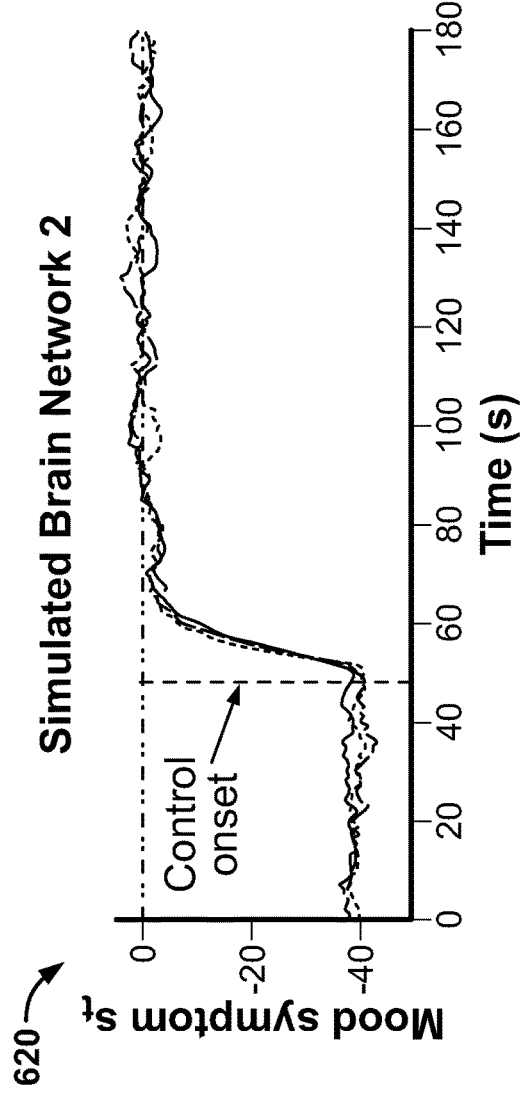
FIGS. 6C-D parallel FIGS. 6A-B, for a second brain network.
Figure 6D:
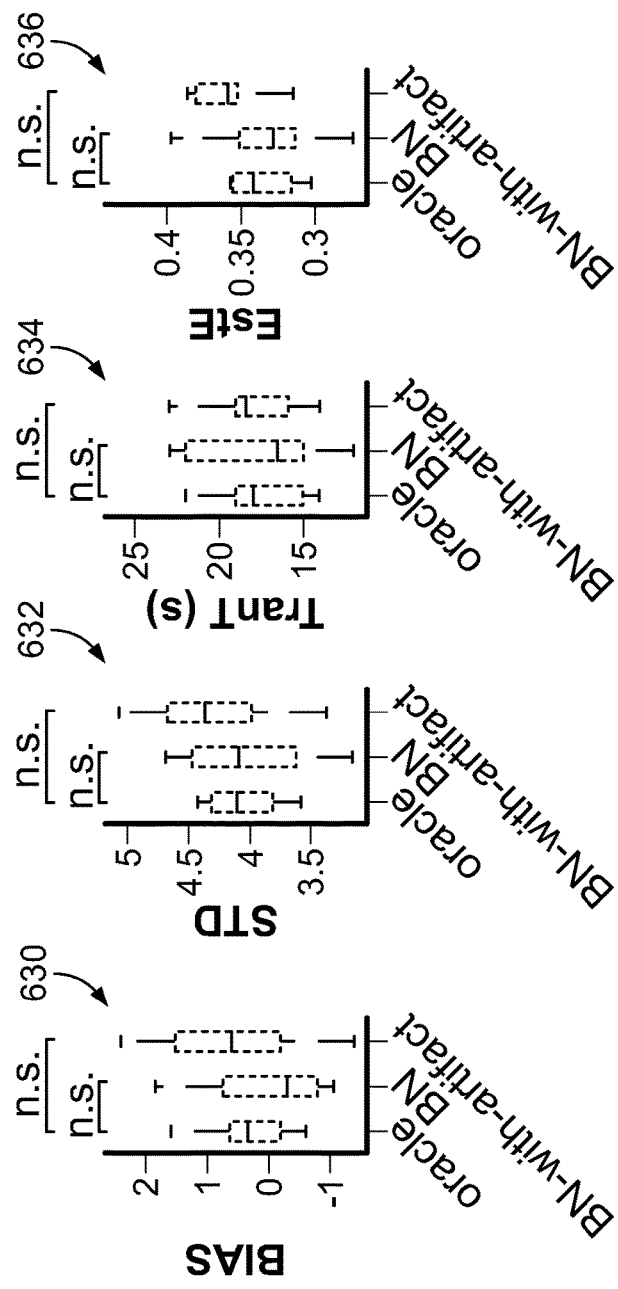

Simulation of a more practical case where there existed stimulation artifacts in the simulation testbed, as described herein above, showed continued accurate performance of the BN Controller. By implementing real-time artifact removal in the controller (PC2, FIG. 3C) for both Simulated Brain Networks 1 and 2, the controlled mood symptom followed the target closely as shown in FIGS. 6A, 6C, and were again close to the mood symptom controlled by the oracle controller. Across the 10 closed-loop simulation trials, there existed no significant differences between the BN-with-artifact controller and the oracle controller for both Simulated Brain Networks as shown in FIG. 6B (Simulated Brain Network 1, BN-with-artifact v.s. oracle, Wilcoxon rank-sum tests, P>0.2 for all performance measures) and in FIG. 6D (Simulated Brain Network 2, BN-with-artifact v.s. oracle; Wilcoxon rank-sum tests, P>0.15 for all performance measures).

Results: GBN-Modulated DBS Waveform Reduced System-Identification Time: Neuro Omega™ Simulations.

Results above demonstrate that BN-modulated DBS waveform enables accurate system-identification and closed-loop control when the identification period is long (T=120 mins). However, there may be constraints on how long the brain can be stimulated in open-loop for system-identification. Tests of how GBN-modulated DBS waveform may improve BN-modulated DBS waveform for time-constrained scenarios where T was restricted to be short (20 mins) were conducted. Simulations in the simulation testbed with Neuro Omega™ were used to compare the BN-20 mins controller and the GBN-20 mins controller, where stimulation artifacts were added in both open-loop system-identification and closed-loop DBS control.

Figure 7A:
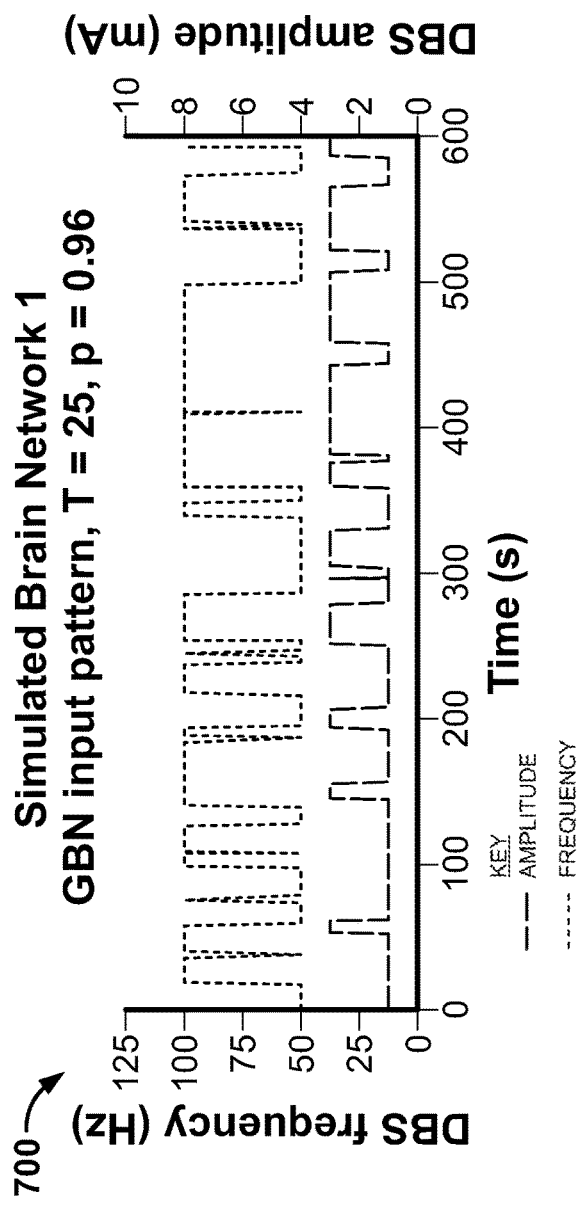
FIG. 7A shows the GBN pattern for the GBN controllers in a Neuro Omega™ simulation with a time-constrained scenario, for a first brain network.
Figure 7B:
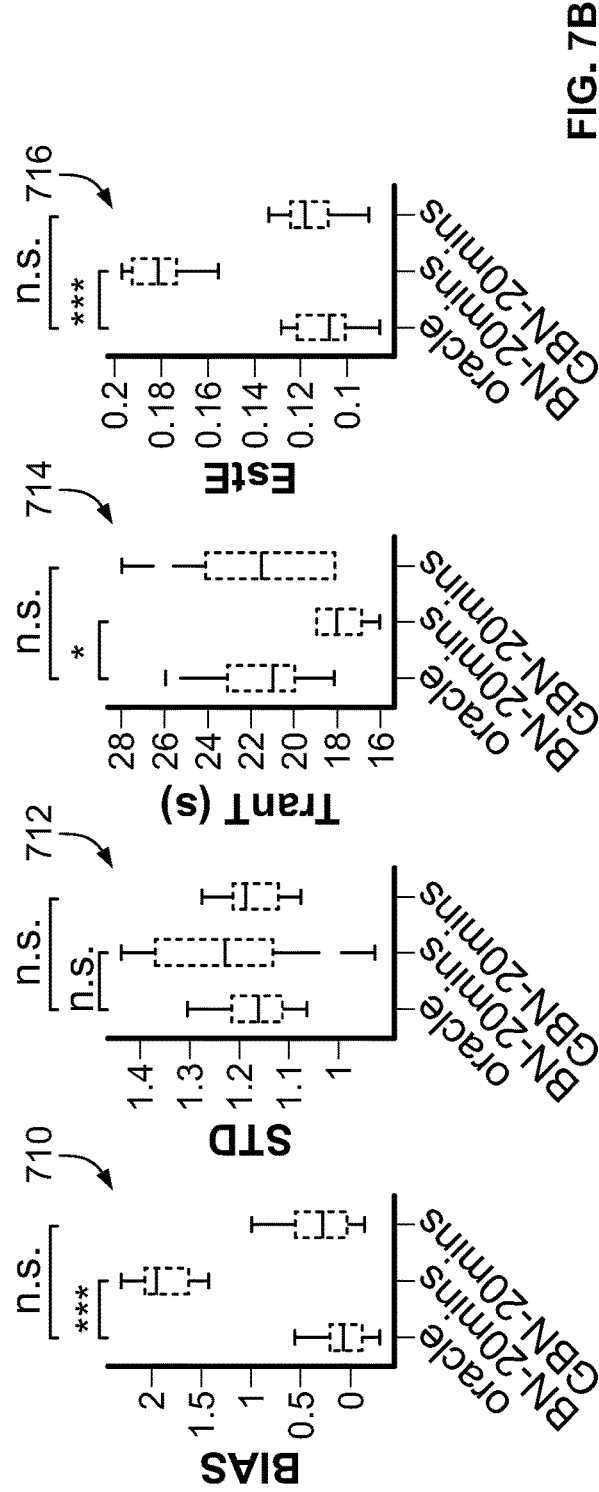
FIG. 7B shows boxplots comparing results for different measures across 10 trials of GBN controller in FIG. 7A with a BN controller and an oracle controller and target in a Neuro Omega™ simulation with a time-constrained scenario, for a first brain network.
Figure 7C:
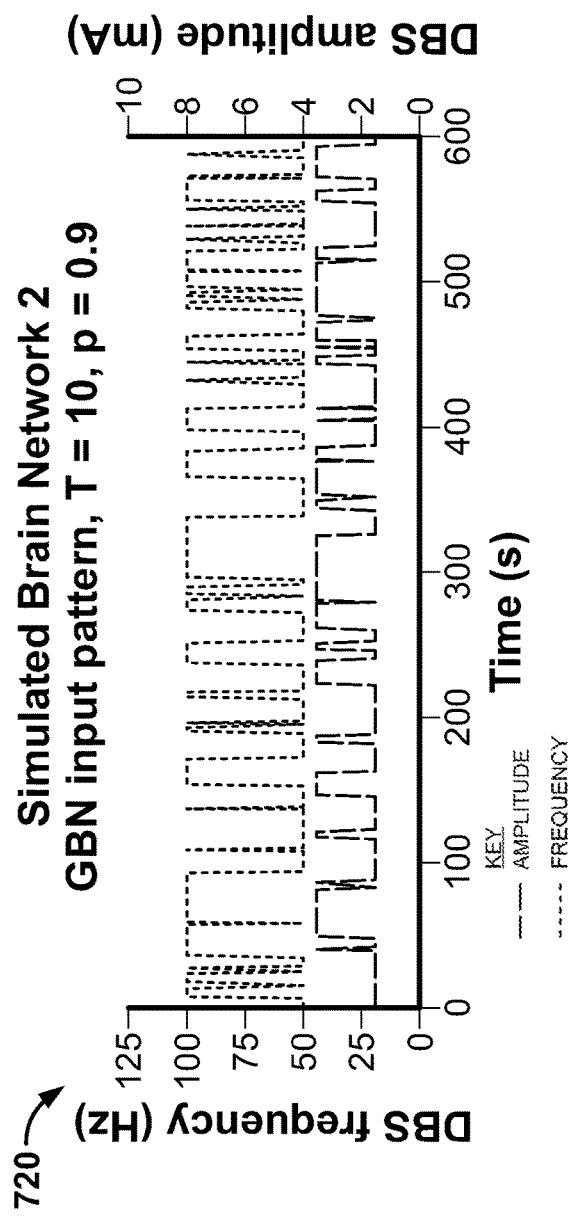
FIGS. 7C-D parallel FIGS. 7A-B, for a second brain network.

The BN-20 mins controller was tested in Simulated Brain Network 1. Its steady-state bias, transition time and neural signature estimation error were significantly worse than the oracle controller across the 10 closed-loop control trials as shown in boxplots 730, 732, 734 and 736 of FIG. 7B (BN-20 min v.s. oracle; Wilcoxon rank-sum tests: BIAS P=1.8×10⁻⁴, TranT P=0.006 and EstE P=1.8×10⁻⁴). The GBN-20 mins controller using an input pattern for different time constants as shown in charts 700, 720 FIGS. 7A, 7C. The time constant of the underlying network dynamics was estimated using a 2 mins on-off stimulation (see disclosure above, note this extra time was much shorter compared with the previous 120 min BN-modulated DBS waveform). The estimated network time constant ($\hat{T}_c$) was 25 s. In comparison, the true time constants corresponding to the four poles of the LSSM used in Simulated Brain Network 1 were 32.8 s, 19.5 s, and 13.7 s=$-1/\ln(p_R)$, where $p_R$ is the real part of a pole), with an average of 23 s. Hence the time constant estimate was close to the true average time-constant. Based on this estimate, we designed a GBN with p=1−½s=0.96, consistent with Equation 4 above; GBN pattern shown in FIG. 7A). Compared with oracle controller, GBN-20 mins controller showed no significant difference across the 10 closed-loop control trials as shown in FIG. 7B (GBN-20 mins v.s. oracle; Wilcoxon rank-sum tests: P>0.25 for all performance measures).

The reason for suboptimal performance of the BN20 mins controller is that the underlying brain network was dominated by slow dynamics. Hence BN was changing too frequently compared with the inherent dynamics. This led to poor excitation and estimation of low frequency components of the dynamics. Inaccurate estimation of $\bar{d}$ resulted in large steady-state bias; inaccurate estimation of T resulted in a poor estimation of the neural signature and further influenced the transition time via the control cost function. Compared with the BN input pattern with p=0.5 (FIG. 2A), the GBN input pattern had p=0.96 and thus made changes much less frequently (FIG. 7A), resulting in more low frequency components. This led system-identification to weigh the low frequency bands more. These bands largely coincided with the important dynamics of the underlying brain network, leading to more accurate model estimation than was possible in the BN-20 mins case.

Figure 7D:
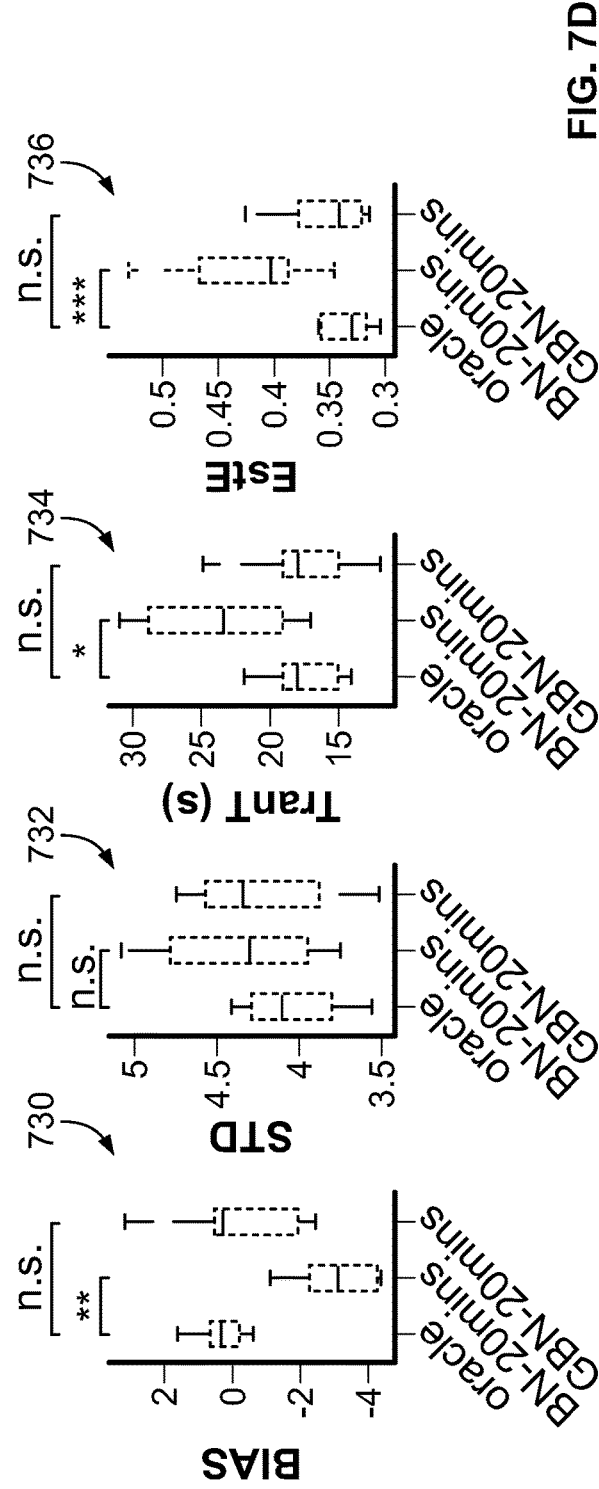

Simulated Brain Network 2 was similarly tested, wherein the BN-20 mins controller also had degenerated performance and performed significantly worse than the oracle controller across the 10 closed-loop control trials, as shown in boxplots 730, 732, 734, 736 of FIG. 7D (BN-20 min v.s. oracle; Wilcoxon rank-sum tests: oracle v.s. BN-20 mins: BIAS P=0:0017, TranT P=0:0150 and EstE P=0:0073). An estimated network time constant of 10 s was obtained from a 3 mins on-off stimulation, which was close to the average time constants of the four poles (9.68 s). Therefore, for Simulated Brain Network 2, GBN took parameter p=1−1=10=0:90 (Eq. 4). The GBN pattern is shown in chart 720, FIG. 7C. Consistent with the results for Simulated Brain Network 1, the closed-loop performance of the GBN-20 mins controller was similar to the oracle controller across the 10 closed-loop control trials as shown in FIG. 7D (GBN-20 mins v.s. oracle; Wilcoxon rank-sum tests: P>0:3 for all performance measures).

Results: BN Controller was Robust to Unknown Mood Disturbance Levels: Neuro Omega™ Simulations.

The robustness of the proposed system-identification framework to unknown levels of inherent depressed mood was examined. Six closed-loop experiments were ran with the Neuro Omega™ simulation testbed under various mood disturbance levels, stimulation artifacts were also simulated. In system-identification, a BN-modulated DBS waveform with T=120 mins was implemented.

Figure 8A:
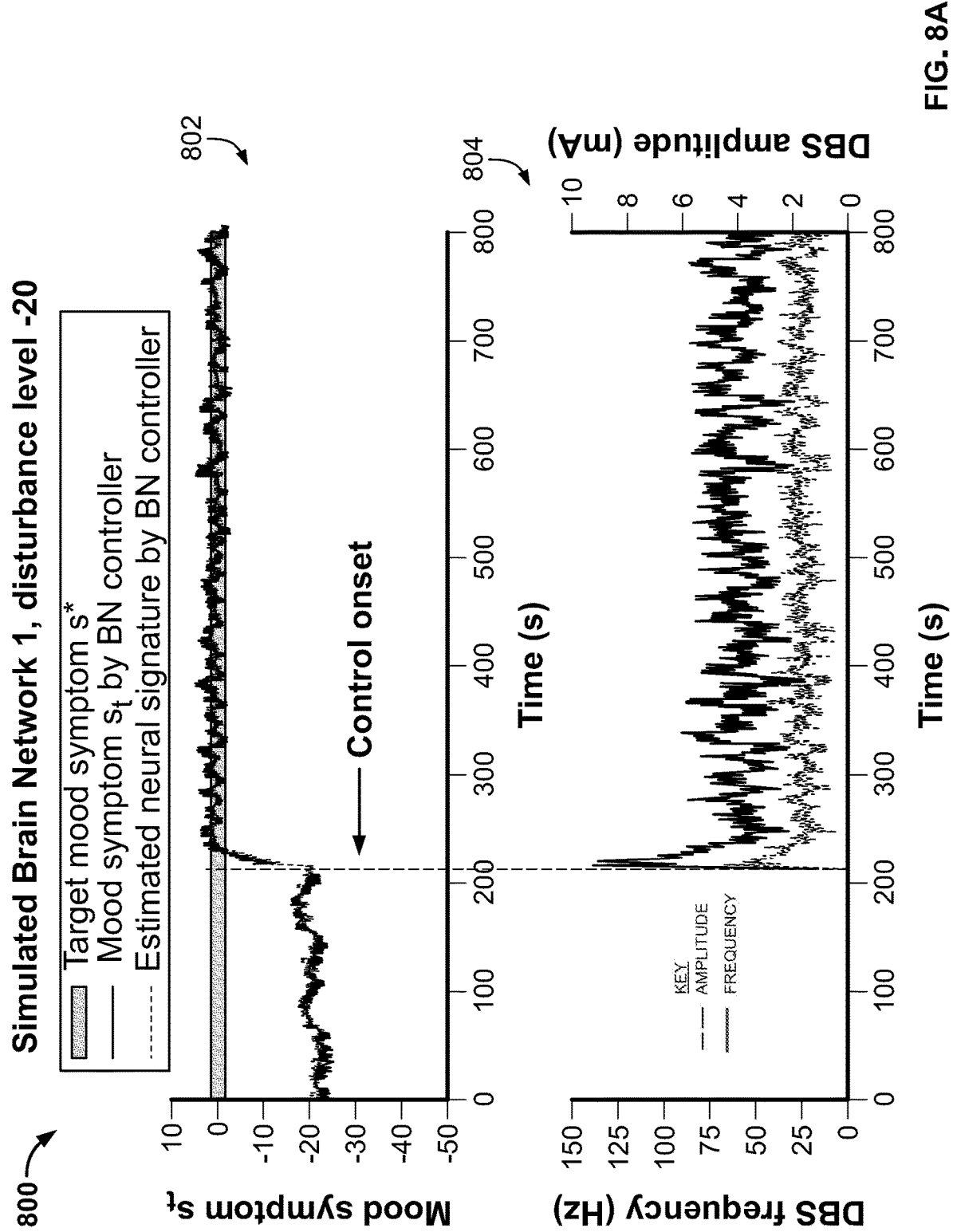
FIGS. 8A-F are charts comparing three different scenarios in two different simulated brain networks, showing robustness of a BN controller to unknown mood disturbance levels.
Figure 8B:
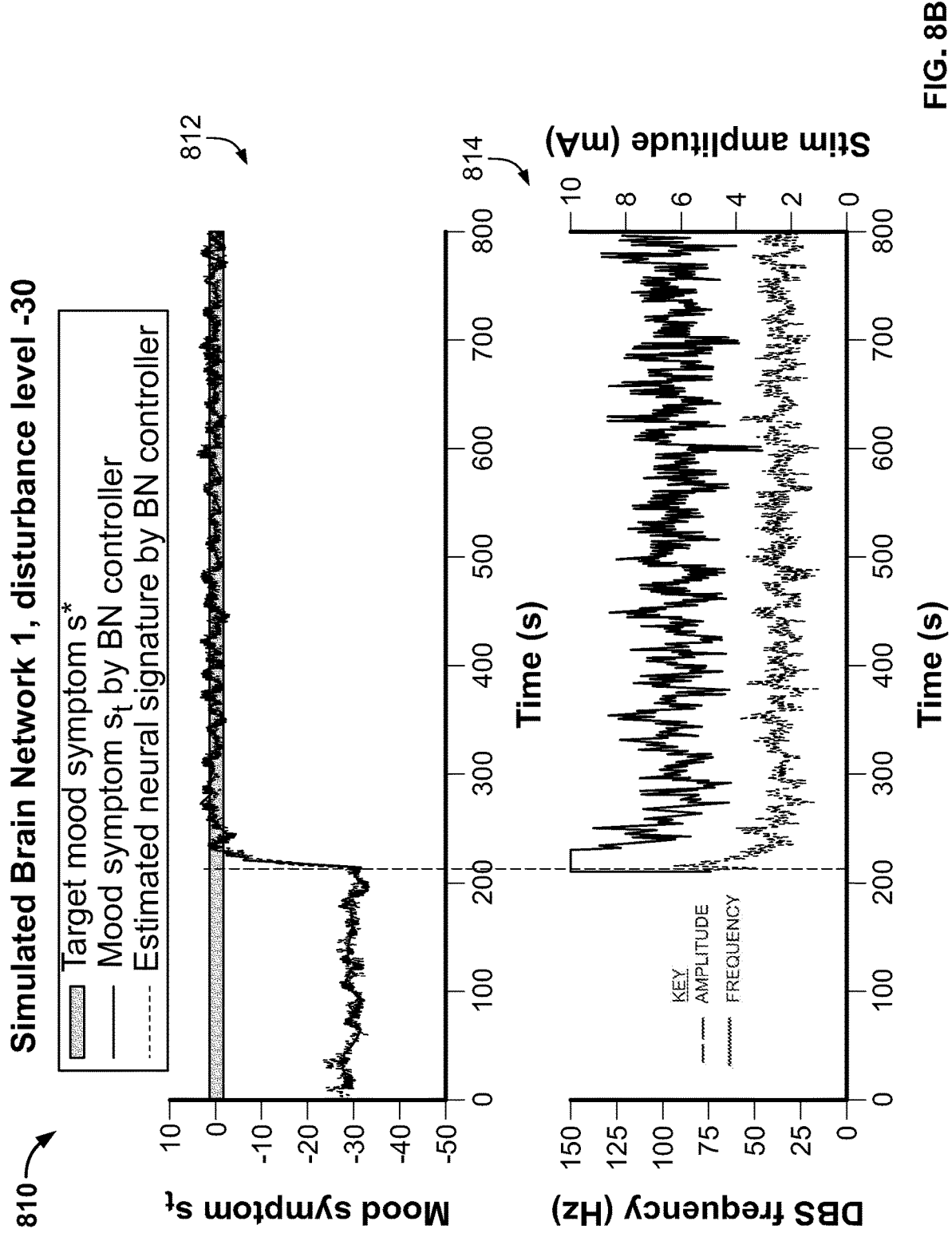
Figure 8C:
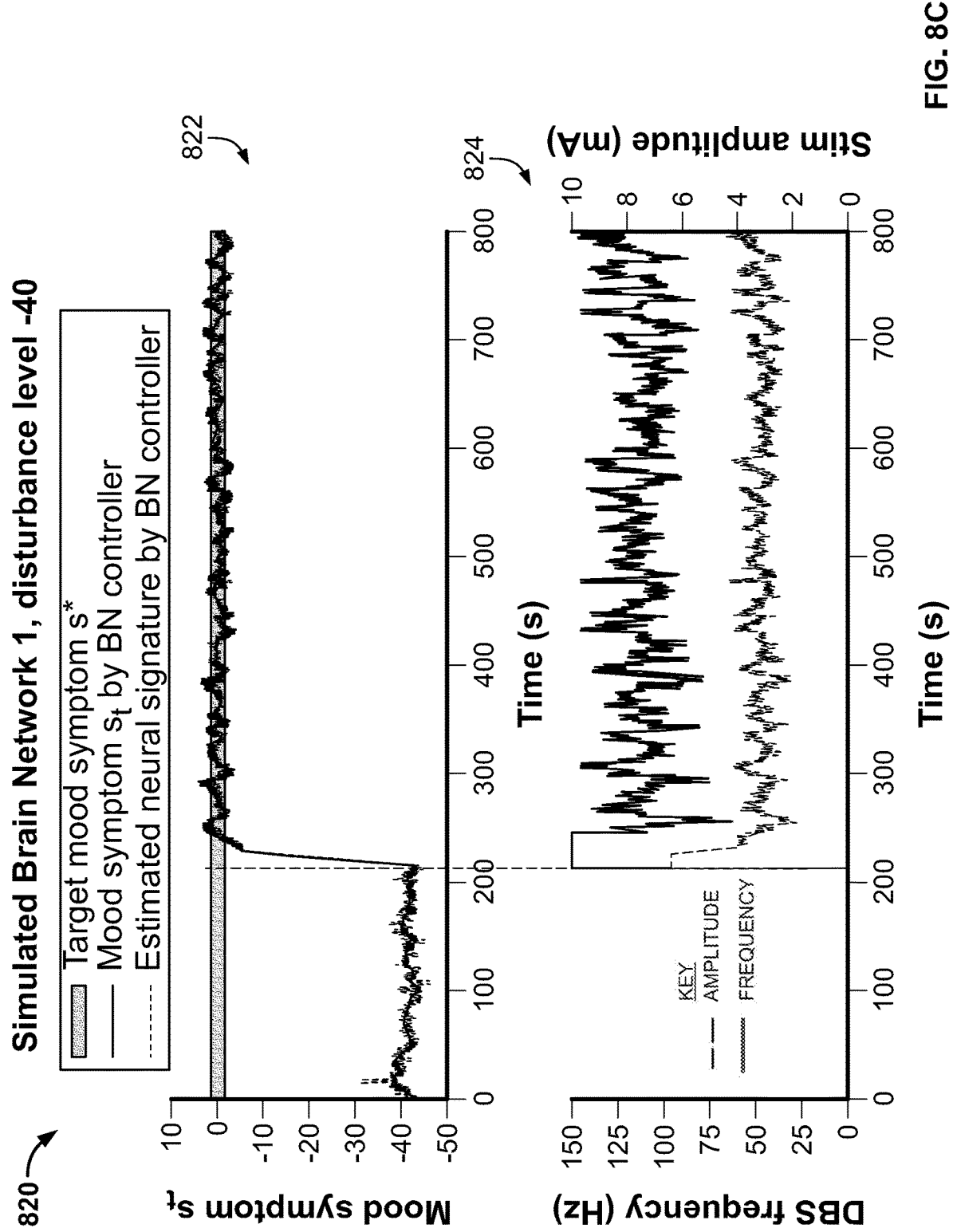
Figure 8D:
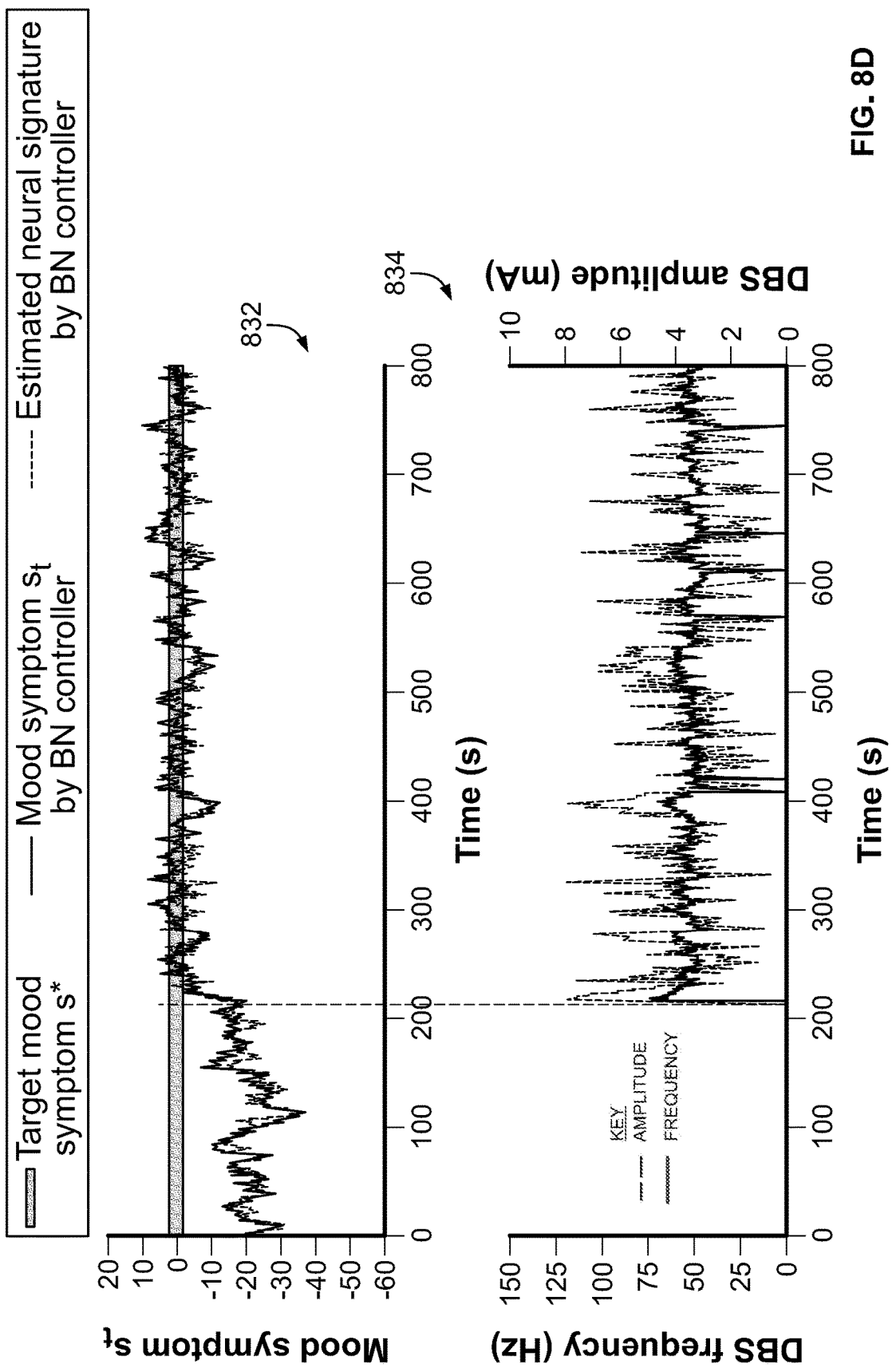
Figure 8E:
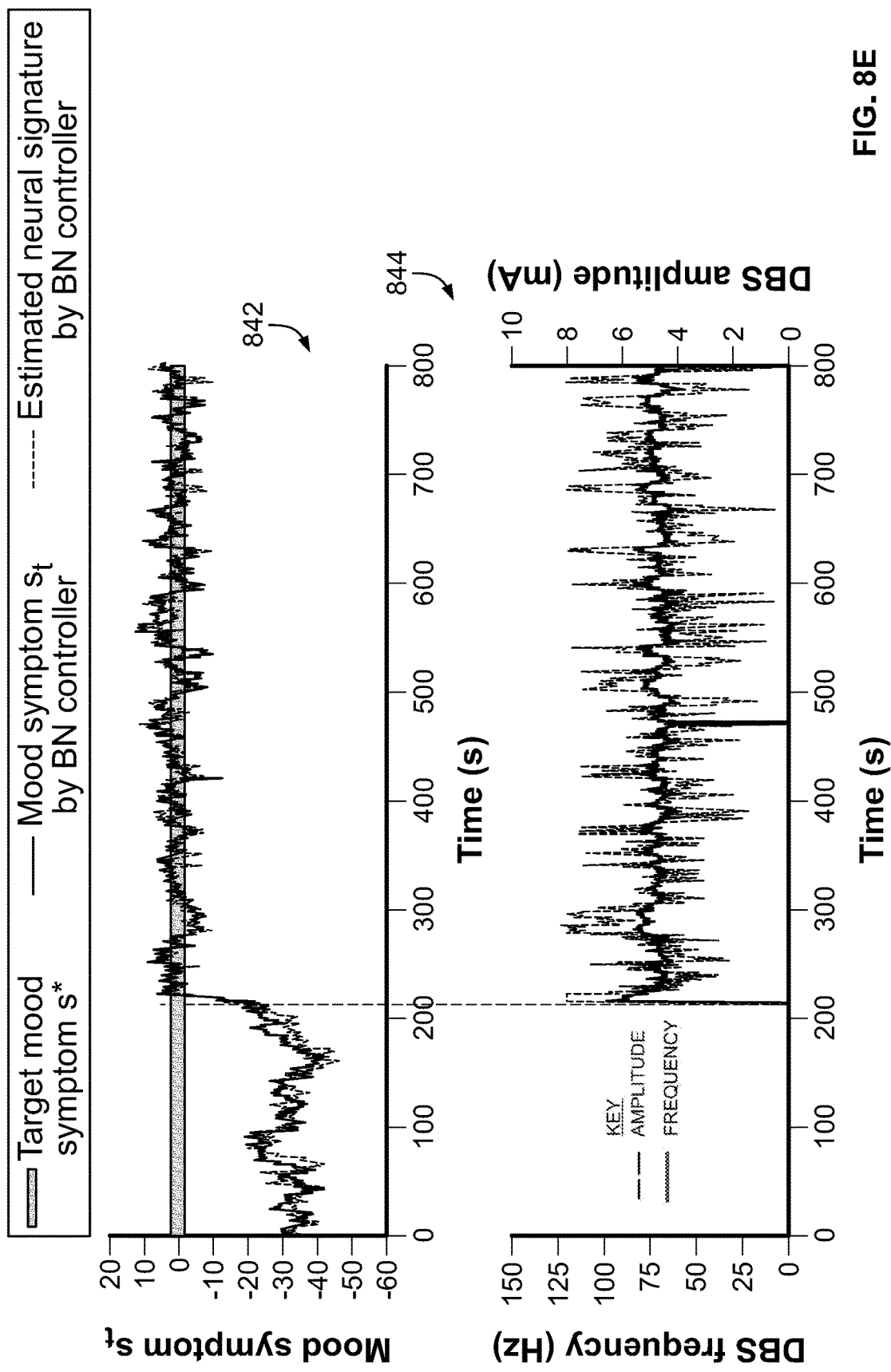
Figure 8F:
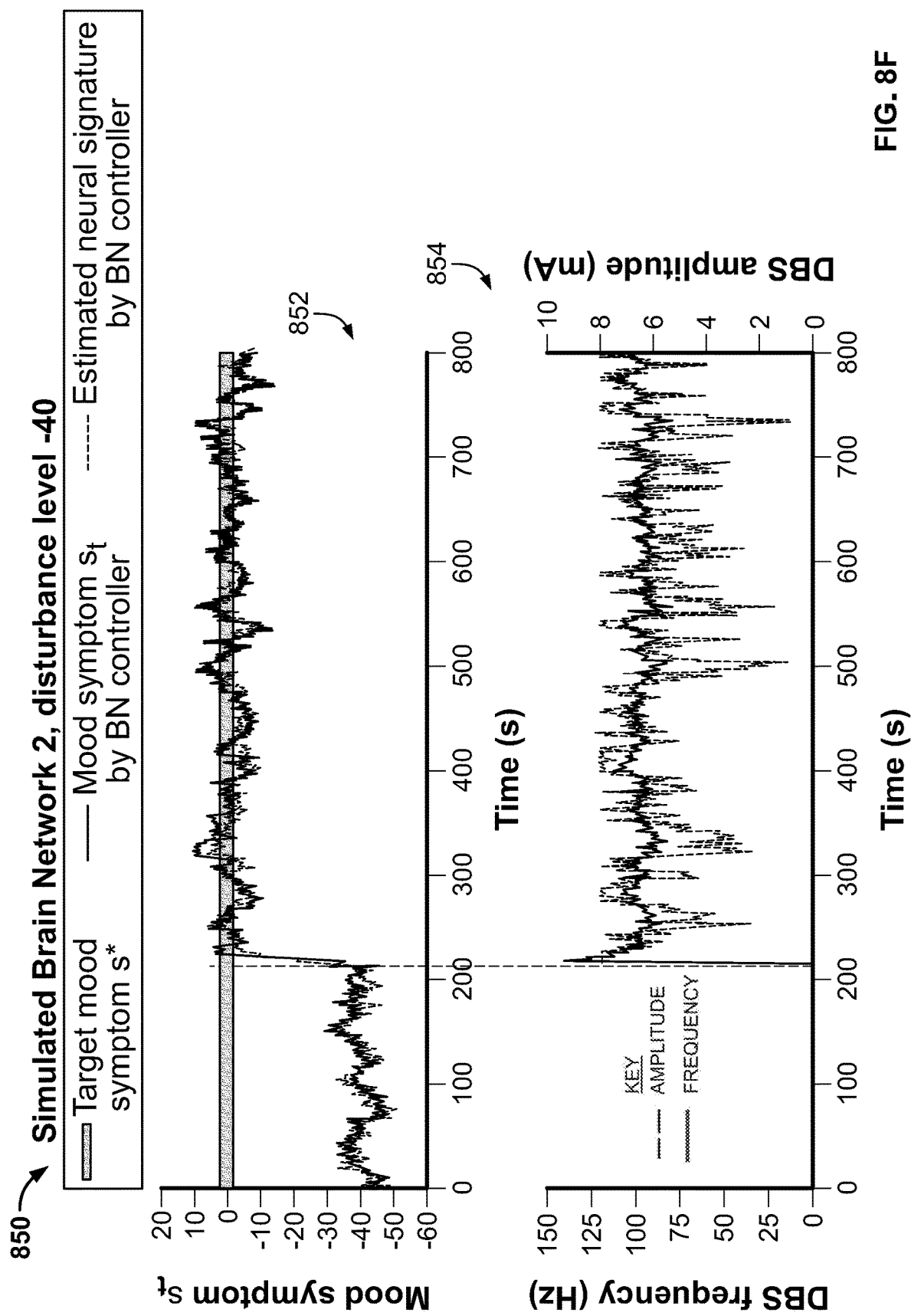

For both Simulated Brain Network 1 and Simulated Brain Network 2, we simulated three scenarios, with $s_{depression}$=−20, −30, −40, representing a progression from less depressed patients to more depressed patients. Each of these closed-loop control sessions lasted for 800 s, where the first 210 s were stimulation off, followed by 590 s where closed-loop stimulation was on. The BN controller achieved transitions without overshoot and precise control of the mood symptom at steady-state across these 6 simulations. A first simulation is shown in charts 800 of FIG. 8A, with chart 802 showing mood symptom control and chart 804 showing DBS frequency over time (1$^{st}$ Brain Network, disturbance level −20). FIG. 8B similarly shows in charts 810, 812, 814 a second simulation for the 1$^{st}$ Brain Network, disturbance level −30. FIG. 8C shows in charts 820, 822, 824 a third simulation for the 1$^{st}$ Brain Network, disturbance level −40. A fourth simulation for the Simulated Brain Network 2, disturbance level −20, is shown charts 830 of FIG. 8D with chart 832 showing mood symptom control and chart 834 showing DBS frequency over time. FIG. 8E similarly shows in charts 840, 842, 844 a fifth simulation for the 2nd Brain Network, disturbance level −30. FIG. 8F shows in charts 850, 852, 854 a sixth simulation for the 2nd Brain Network, disturbance level −40. In addition, the estimated neural signature $\hat{s}_t$ followed closely the true mood symptom $s_t$ (see FIGS. 8A-F). By comparing the charts in FIGS. 8A-F across columns, we see that the BN controller was robust to different levels of unknown mood disturbances. By comparing the subfigures in FIGS. 8A-F across rows we see that the BN controller was robust to different underlying brain networks.

Discussion/Summary.

A new computational framework has been presented herein to model and identify IO dynamics of brain networks in response to electrical stimulation. Implementation of a real-time clinical closed-loop simulation testbed using Neuro Omega™ is used to validate the framework. In the computational framework, 1) general LSSMs are built to describe the IO dynamics, identify a low-dimensional brain state, and enable closed-loop control, 2) a new open-loop input DBS/stimulation waveform—a pulse train modulated by BN parameters, or BN input patterns that is both critical for model identification and consistent with current DBS safety conventions is developed and tested, and 3) the BN-modulated DBS waveform is generalized to a GBN-modulated DBS waveform to reduce the time needed for open-loop brain stimulation to identify the models. In the closed-loop testbed, apparatus and methods are described for (i) open-loop system identification using the (G)BN-modulated DBS waveform, and (ii) closed-loop control of the brain network. The present disclosure uses depression as an example, but other brain states may similarly be controlled. Within this testbed, stochastic noises, unknown disturbances, and stimulation artifacts to simulate were incorporated as closely as possible to a real-world scenario and resulting robustness was assessed.

The modeling framework was validated by two sets of experiments: (i) open-loop system-identification experiments to assess closeness of the estimated model in the Neuro Omega™ testbed to the true brain network model, and (ii) closed-loop control experiments to evaluate mood symptom control in depression within this testbed. It was shown that 1) the novel design of the BN input pattern is critical for accurate identification of brain networks; the proposed BN input pattern achieved accurate model parameter identification, outperforming other suboptimal input patterns; 2) the novel design of the BN input pattern is critical for accurate closed-loop control of brain networks; in contrast to other input patterns, the closed-loop controller built from BN identification achieved tight control of the mood symptom, with a steady-state and transient performance similar to the best possible performance (oracle controller); 3) to enable short open-loop brain stimulation for model identification, the new GBN input pattern can improve the performance of the BN input pattern by incorporating the time-constant information of the brain network; this time-constant information can in turn be estimated in a short on-off stimulation session.

LSSM as a Model Structure for Brain Network IO Identification and Closed-Loop Control.

In the present disclosure, LSSMs are used to describe the IO dynamics of brain networks to enable the design of closed-loop DBS systems. While neuronal dynamics are in general nonlinear, there are multiple reasons to select an LSSM for the purpose of closed-loop DBS.

First, closed-loop DBS requires the use of IO models that are amenable to efficient identification, and for which performance guarantees can be provided for safety. This is especially the case given the high-dimensional neural recordings (e.g., hundreds of ECoG recording electrodes) that need to be modeled and used as feedback in many DBS applications. LSSM provides a model structure that satisfies these conditions. Design of a novel (G)BN-modulated DBS waveform for brain network IO identification was accomplished by combining the requirements for DBS waveforms and the theoretical requirements that exist for LSSM model identification (i.e., white spectrum inputs). This is in contrast to nonlinear models for which there exist no such global guarantees, hindering an optimal DBS input design. In addition, to estimate LSSMs, projection and subspace identification algorithms can be exploited, which are numerically more stable and have lower computational burdens than recursive identification algorithms for nonlinear systems, e.g., prediction-error-methods. The high-dimensional and large amount of identification data can cause both stability and computation burden problems for nonlinear system identification.

Second, a brain network IO model for DBS should be amenable to closed-loop control. LSSM is a powerful model structure that allows optimal closed-loop controller design. Many well-established estimation (e.g., Kalman estimator, robust H∞ estimator) and control (e.g. linear-quadratic-regulator, model predictive control) algorithms can be used for LSSMs; these designs have led to successful closed-loop controllers for numerous industrial processes despite their potential inherent non-linearity. Computational neural network models consisting of nonlinear neural oscillators have been used in simulations to study the effects of open-loop high frequency DBS, or to explore possible closed-loop DBS strategies. However, these models are not suitable for robust and accurate closed-loop controller design. For example, simulations show that based on nonlinear IO models, the choice of feedback gain that guarantees closed-loop stability could only be obtained through trial and error simulations since no closed-form solutions existed. In contrast, LSSM modeling can lead to an efficient and practical approach to model the dynamics of electrophysiological time-series (e.g., spiking rates, LFP and ECoG) and the effect of DBS on these dynamics; this in turn enables the development of closed-loop controlled DBS systems.

Third, linear models have been used to describe spontaneous (i.e., without external input) neural dynamics at the large macroscopic scale of neural populations, e.g., electroencephalography (EEG) or magnetoencephalography (MEG). More specifically, even though cell level neuronal dynamics are highly nonlinear, macroscopic level spontaneous neural activity emerging from complex collections of numerous nonlinear neuronal dynamic processes can be described by linear models for different purposes. Linear autoregressive models have been built to study EEG dynamics, and linear models used to characterize MEG dynamics for estimation of brain source current. Linear models have also been used to quantify rotational spontaneous neural dynamics during reaching behaviors. While a goal includes modeling the input-output neural dynamics in response to DBS rather than spontaneous neural dynamics, these prior studies provide evidence that linear models could also be sufficient for IO identification.

Finally, there are two flexible design choices that can further mitigate the effect of potential nonlinearities on the present modeling framework. First, we have the flexibility to pick the model order. It is well-known that picking a linear model of higher order can sufficiently capture nonlinear dynamics in many cases. Second, we can use a time-varying piece-wise linear model instead of a time-invariant linear model. In this case, we would divide the DBS parameter space into several regimes, build a different linear model for each regime, identify these models using BN input patterns with appropriate DBS parameters within these regimes, and finally derive piece-wise linear models and feedback controllers. Finally, it is well-known that feedback control linearizes a nonlinear system, further making the case for the use of LSSM for the purpose of closed-loop control.

BN-Modulated DBS Waveform for Identification of Brain Network IO Dynamics.

System-identification is a crucial component in designing model-based controllers that interact with the brain. For example, as shown in closed-loop BMIs for anesthesia control, or in closed-loop motor BMIs. Data-driven open-loop system identification requires informative IO datasets. This critically requires an optimal input signal design. In traditional linear industrial and chemical process identification, BN inputs have been used since they have white spectrum and are convenient to operate. BN behavioral input stimulus have also been used to study biological systems such as the auditory nervous system, the horizontal vestibuloocular reflex system and the motor system.

To enable identification of brain network IO dynamics in response to DBS, and consequently to develop closed-loop DBS systems, we designed a novel open-loop DBS waveform by utilizing the concept of BN. The DBS waveform needs to be charge-balanced in a short time and hence typically must consist of biphasic pulses. Moreover, it is the DBS parameters such as pulse amplitude and frequency that affect neural and clinical outcomes. Hence a direct BN DBS waveform is not useful for brain stimulation. The main innovation in designing BN-modulated DBS waveform is that the neural dynamics be related to DBS parameters instead of the DBS waveform itself by designing a pulse train whose DBS parameters are stochastically changed according to a BN sequence. This waveform can incorporate as its building block any conventional DBS pulse shape such as monophasic or biphasic pulses, or even specialized DBS pulse shapes that can reduce stimulation artifact duration. This flexibility allows the BN-modulated DBS waveform to generalize across applications given that different pulse patterns can lead to different DBS effects.

BN-modulated DBS waveform may require a long identification time in some scenarios. However, the duration of open-loop brain stimulation to identify models should be restricted for practical and safety reasons. The BN-modulated DBS waveform is thus extended to a GBN-modulated DBS waveform by estimating the time-constant of the underlying brain network, and using this estimate in the selection of the switching probability of the waveform parameters. This new DBS waveform allows for a significant reduction in identification time without a cost on accuracy.

Towards Clinical Closed-Loop DBS Experiments.

The proposed LSSM modeling and BN identification methods have been verified by developing a real-time closed-loop BMI simulation testbed using the clinical Neuro Omega™ microelectrode recording and stimulation system. This new simulation testbed allows for extensive simulations that are essential to ensure reliability and safety before moving towards clinical human experiments. Numerical simulations have also been used to test several closed-loop DBS designs. However, these prior work only carried out computer program simulations and did not implement a testbed using an actual clinical neurophysiological recording and stimulation system. To enable realistic simulations, we built this testbed using the same clinical system that would be used in human experiments, and incorporated in our simulations stochastic noises, disturbances, time-delays, and recording stimulation artifacts that are difficult to mimic purely using computer program. This closed-loop DBS system fully ensembles a real clinical scenario except that the ECoG signal was generated by a simulated brain network rather than a human brain. While the testbed was used for validation of the LSSM modeling and BN identification frameworks, the testbed itself is general and can be used to simulate closed-loop treatment of other neural disorders by changing the simulated brain model accordingly, e.g., using the nonlinear models used for PD or epilepsy.

By validating the performance of BN identification and the corresponding closed-loop controller within the clinical simulation testbed, this work paves the way for active efforts to develop effective closed-loop treatments for neurological disorders such as depression and anxiety and implementing them in human clinical experiments. Two important directions towards clinical testing may be pursued:

(i) Identification of network neural signatures for various neurological disorders. Neural signatures relate neural dynamics to patient behavioral symptoms, and are necessary feedback signals for closed-loop control. There has been extensive work in studying abnormal neural oscillations or couplings for epilepsy, Parkinson's disease and dystonia. However, the mechanisms underlying these abnormal neural activities and the choice of a neural signature are still under extensive investigation. Moreover neural signatures for other neurological disorders such as neuropsychiatric disorders including depression and anxiety are largely unknown. The LSSM modeling framework proposed here can characterize neural dynamics at the network level. Hence it is important to investigate whether LSSM modeling can identify neural signatures for neurological disorders such as mood disorders including depression and anxiety.

(ii) BN identification and model-based closed-loop control in animals and humans. Having established the performance of the proposed methods in a clinical simulation testbed, a next step is to apply BN stimulation in animal and human subjects using the exact protocol used in the Neuro Omega™ simulations presented herein. The new BN IO identification framework allows investigation of the effect of electrical stimulation on neural activity and the neural signatures of disease. The identified IO model will both facilitate deeper understanding of the dynamics of brain networks, and better design of closed-loop controllers.

In an aspect, the use of BN/GBN waveforms as described herein for brain stimulation can also be applied to non-electrical stimulation inputs such as for example optogenetic stimulation. For optogenetics the parameters to switch over are for example the rate and/or width and/or amplitude of the light pulses. Other aspects of BN/GBN identification and use of the identified waveform for closed-loop control may otherwise be as described herein for electrical stimulation, when applied to optogenetic stimulation.

Kalman Filter and LQR Controller Design.

The Kalman estimator gives optimal estimate of $x_t$ via the following recursion $$\begin{cases} \hat{x}_{(t+1|t)} = A\hat{x}_{t|t} + Bu_t + B\bar{d} \\ \hat{x}_{(t+1|t+1)} = \hat{x}_{t|t} + L(y_{t+1} - C\hat{x}_{t|t} - Du_t - D\bar{d}) \end{cases} \quad (11)$$

where the gain matrix L is the solution of the algebraic Riccati equation [53] (given that the pair [A,C] is observable) $L=PC^TR^{-1}-PC^T(CPC^T+R)CPC^TR^{-1}$, where the matrix P satisfies the Ricatti equation $P=APA^T+Q-(APC^T+S)(CPC^T+R)^{-1}(CPA^T+S)$. Here, we set the initial estimate as $\hat{x}(-1|-1)=0$.

The LQR controller takes as feedback the Kalman state estimate and decides on the simulation parameters $u_t$ to take the diseased brain state to a healthy level, which we quantify in terms of the neural signature as $s^*=0$. LQR algorithm minimizes the quadratic cost function $$J(u_t)=\Sigma_{t=0}^{\infty}x_t^TT^TTx_t+(u_t-u^*)^TR_w(u_t-u^*) \quad (12)$$

where $u^*$ is the steady-state stimulation parameters required to maintain the target level $s^*=0$, and $R_w$ is a positive definite matrix chosen depending on the desired system response. The optimal solution of $u_t$ is given by a linear feedback of the state $$u_t=-Gx_t+u^* \quad (13)$$

The feedback gain G is given by the Riccati equation solution (given that the pair [A,B] is controllable), $G=(R_w+B^THB)^{-1}B^THA$, where H satisfies the Riccati equation $H=A^THA+T^TT-A^THB(R_w+B^THB)^{-1}B^THA$. Also, it's easy to verify that to keep $s^*=0$, the sufficient condition is $u^*=\bar{d}$. In addition, we impose the constraint of positivity of the control variables by bounding the solution in (13). In online implementation, the value of $x_t$ is given by the state estimate $\hat{x}_{t|t}$ in (11). Also we note that in all simulations, we select the LQR weighting matrix as $$R_W = \begin{bmatrix} 10^{-3} & 0 \\ 0 & 10^{-2} \end{bmatrix}.$$

Identification of Unknown Disturbance $\bar{d}$.

We estimate $\bar{d}$ based on $$O^T = \{s_t, y_t\}_{t=0}^{T-1}.$$

At steady state, the contribution of the constant disturbance is on the mean of $s_t$ and $y_t$. Hence, we take the mean of both sides in (5) and get $$\bar{x}=A\bar{x}+B\bar{u}+B\bar{d}$$

$$\bar{y}=C\bar{x}+D\bar{u}+D\bar{d}$$

$$\bar{s}=T\bar{x}$$

In this data set, we have $u_t=0$. Plugging this into the above equations, and by rearranging the variable, we have the following set of linear equations with known variables $\bar{s}$ and $\bar{y}_t$ and unknown variables $\bar{x}$ and $\bar{d}$:

$$\begin{bmatrix} A-I & B \\ C & D \\ T & 0 \end{bmatrix} \begin{bmatrix} \bar{x} \\ \bar{d} \end{bmatrix} = \begin{bmatrix} 0 \\ \bar{y} \\ \bar{s} \end{bmatrix}$$

Then, we estimate the constant disturbance as the minimum-norm or least-squares solution of the above equations.

Definition of System Norm $\mathcal{H}_2$.

We first derive an equivalent form of the LSSM (1). Assuming the LSSM (1) is observable, an equivalent description of the input-output (IO) relationship and second order noise statistics is $$x_{t+1} = Ax_t + Bu_t + Ke_t$$

$$y_t = Cx_t + Du_t + e_t \qquad (14)$$

with $K = (APC^T + S)(CPC^T + R)^{-1}$, where matrix P satisfies the Ricatti equation $P = APA^T + Q - (APC^T + S)(CPC^T + R)^{-1}(CPA^T + S)$. In addition, $E[e_i e_j^T] = V\mathcal{S}_{ij}$ where $V = CPC^T + R$. The above LSSM captures two important dynamics in neural activity. The first one is IO dynamics and the second one is noise dynamics. We further describe these two relationships more compactly as follows. By applying $\mathcal{F}$ transform (z-transform) to (14), we have $$zX(z) = Ax(z) + BU(z) + KN(z)$$

$$Y(z) = Cx(z) + DU(z) + N(z) \qquad (15)$$

where $X(z) = \mathcal{F}(x_t)$, $U(z) = \mathcal{F}(u_t)$, $Y(z) = \mathcal{F}(y_t)$, and $N(z) = \mathcal{F}(e_t)$. By solving the first equation for $X(z)$, and plugging the solution into the second equation, we have $$Y(z) = G(z)U(z) + H(z)N(z), \qquad (16)$$

where $$G(z) = C(zI - A)^{-1}B + D, \qquad (17)$$

and $$H(z) = C(zI - A)^{-1}KV^{1/2} + V^{1/2} \qquad (18)$$

Here, we define $G(z)$ as the IO dynamics and $H(z)$ as the noise dynamics. The system norm is then defined as $$\|\mathcal{G}\|_2 = \sqrt{\frac{1}{2\pi} \int_{-\infty}^{\infty} Tr(G(e^{jw})^H G(e^{jw})) d\omega}$$

where $Tr(\cdot)$ denote matrix trace, $^H$ denotes conjugate transpose and $G(z)$ is the IO dynamics. $\mathcal{H}_2$ norm measures the expected root mean-square value of the output of a system in response to white noise excitation. Similarly, for noise dynamics, $$\|\mathcal{N}\|_2 = \sqrt{\frac{1}{2\pi} \int_{-\infty}^{\infty} Tr(H(e^{jw})^H H(e^{jw})) d\omega}.$$

Methods and Apparatus, Further Examples

Figure 9:
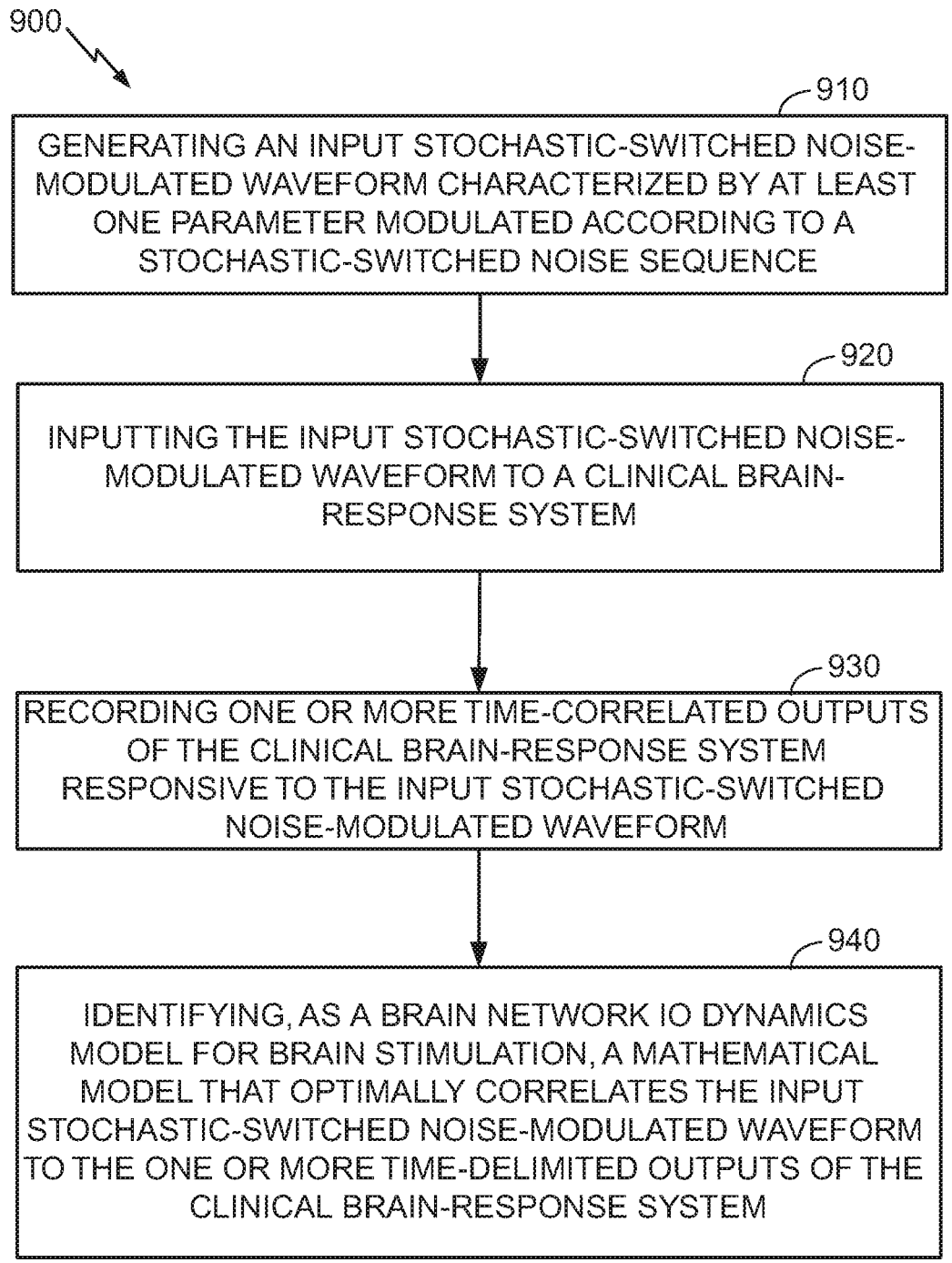
FIG. 9 is a flowchart illustrating aspects of a method for time-efficient identification of a brain network input-output (IO) dynamics model for brain stimulation such as deep brain stimulation.

In summary of the foregoing, FIG. 9 shows aspects of a method 900 for time-efficient identification of a brain network input-output (IO) dynamics model for brain stimulation may include, at 910, generating an input stochastic-switched noise-modulated waveform characterized by at least one parameter modulated according to a stochastic-switched noise sequence. The method may further include, at 920, inputting the input stochastic-switched noise-modulated waveform to a clinical brain-response system. The method may further include, at 930, recording one or more time-correlated outputs of the clinical brain-response system responsive to the input stochastic-switched noise-modulated waveform. The method may further include, at 940, identifying, as a brain network IO dynamics model for brain stimulation, a mathematical model that optimally correlates the input stochastic-switched noise-modulated waveform to the one or more time-delimited outputs of the clinical brain-response system.

In a further aspect, the stochastic-switched noise-modulated waveform is generalized by a tunable parameter based on a ratio of a minimum switching time ($T_{sw}$) to a time constant ($T_c$) for the brain network IO model. For example, the tunable parameter may be determined by $1 - T_{sw}/T_c$ in equation 4. Estimating a value of $T_c$ may be performed, for example, by applying an on-off input pattern to the clinical brain-response system in open loop mode and measuring a rise time for achieving a defined initial portion of a transition period. In an aspect, the defined initial portion may defined by 1/e (36.79%). The estimating may include repeating the applying and the measuring, thereby obtaining multiple values of the rise time, and averaging the multiple values to obtain the value of $T_c$.

In a further aspect, the mathematical model is a linear state-space model. Identifying the model may include, for example, constructing a linear state-space model and determining parameters that most closely fit the observed responses of the clinical system over a specified range of inputs. In an aspect, the clinical brain-response system may be an electronic system that simulates brain response with electrodes, for example, a Neuro Omega™ system as described in connection with FIG. 3A, or a Monte Carlo simulator. In an alternative aspect, the clinical brain-response system may include an electrode implanted in a living brain with the outputs measured by an electrode array, sometimes called a true brain system.

In a further aspect, the stochastic-switched noise-modulated waveform is a binary waveform. The at least one parameter may selected from frequency, amplitude, or pulse width. Examples are provided in connection with FIGS. 2A-D, and elsewhere herein. As used herein, "stochastic switched" means that the value of each waveform parameter (e.g., frequency and amplitude) is switched between two or more values at randomly determined intervals. If the switching is between two predetermined values only, the waveform is referred to herein as "binary."

Figure 10:
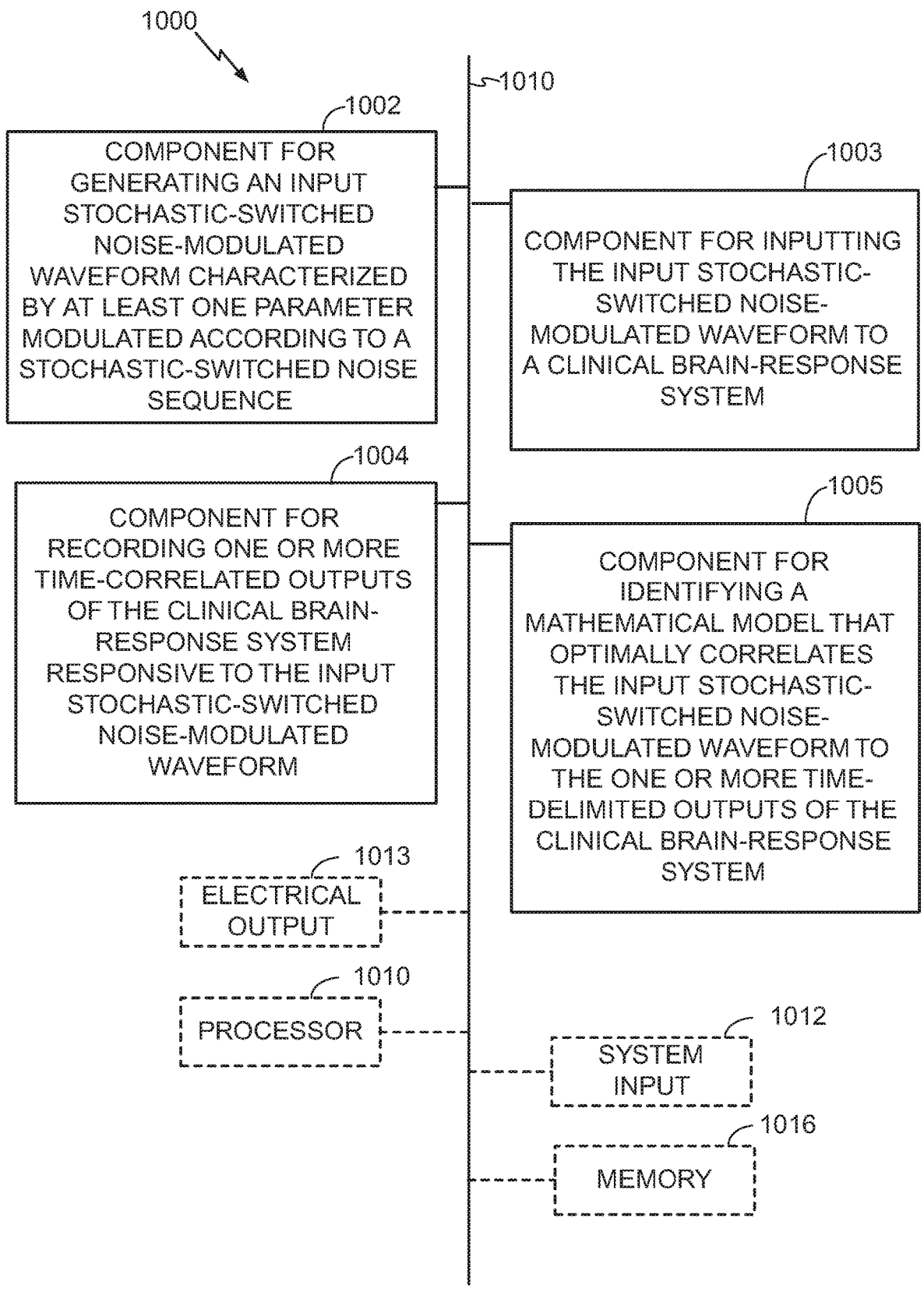
FIG. 10 is a block diagram illustrating aspects of an apparatus for performing the method shown in FIG. 9.

FIG. 10 is a conceptual block diagram illustrating components of an apparatus or system 1000 for time-efficient identification of a brain network input-output (IO) dynamics model for brain stimulation, as described herein. The apparatus or system 1000 may include additional or more detailed components for performing functions or process operations as described herein. For example, the processor 1010 and memory 1016 may contain an instantiation of a process for identifying an I/O model as described herein above. As depicted, the apparatus or system 1000 may include functional blocks that can represent functions implemented by a processor, software, or combination thereof (e.g., firmware).

As illustrated in FIG. 10, the apparatus or system 1000 may comprise an electrical component 1002 for generating an input stochastic-switched noise-modulated waveform characterized by at least one parameter modulated according to a stochastic-switched noise sequence. The component 1002 may be, or may include, a means for said generating. Said means may include the processor 1010 coupled to the memory 1016, to an electrical output 1013 connected to an input of a clinical brain system and to an input 1012 connected to an output of the brain system, the processor executing an algorithm based on program instructions stored in the memory. Such algorithm may include a sequence of more detailed operations, for example, receiving DBS parameters for an input signal (e.g., parameters for BN or GBN input) in a digital data format and generating an analog electrical signal for an electrode array using an D/A signal generator so as to comply with the DBS parameters.

The apparatus 1000 may further include an electrical component 1003 for inputting the input stochastic-switched noise-modulated waveform to the clinical brain-response system. The component 1003 may be, or may include, a means for said inputting. Said means may include the processor 1010 coupled to the memory 1016, the processor executing an algorithm based on program instructions stored in the memory. Such algorithm may include a sequence of more detailed operations, for example, receiving a sequence of digital data representing binary numbers, converting the sequence to a waveform using a digital-to-analog converter, and transmitting the waveform from the output 1013.

The apparatus 1000 may further include an electrical component 1004 for recording one or more time-correlated outputs of the clinical brain-response system responsive to the input stochastic-switched noise-modulated waveform. The component 1004 may be, or may include, a means for said recording. Said means may include the processor 1010 coupled to the memory 1016 and to the input 1012, the processor executing an algorithm based on program instructions stored in the memory. Such algorithm may include a sequence of more detailed operations, for example, receiving one or more analog signals, converting the signals to digital number sequences using an analog-to-digital converter, and storing the sequences in a memory correlated by a time index to each other and to the output sequence.

The apparatus 1000 may further include an electrical component 1005 for identifying, as a brain network IO dynamics model for brain stimulation, a mathematical model that optimally correlates the input stochastic-switched noise-modulated waveform to the one or more time-delimited outputs of the clinical brain-response system. The component 1005 may be, or may include, a means for said identifying. Said means may include the processor 1010 coupled to the memory 1016, the processor executing an algorithm based on program instructions stored in the memory. Such algorithm may include a sequence of more detailed computational operations, for example, as described in connection with FIGS. 1A-B and 3D for system identification.

The apparatus 1000 may optionally include a processor module 1010 having at least one processor. The processor 1010 may be in operative communication with the modules 1002-1005 via a bus 1010 or similar communication coupling. In the alternative, one or more of the modules may be instantiated as functional modules in a memory of the processor. The processor 1010 may effect initiation and scheduling of the processes or functions performed by electrical components 1002-1005.

In related aspects, the apparatus 1000 may include a network interface module (not shown) operable for communicating with system components over a computer network. A network interface module may be, or may include, for example, an Ethernet port or serial port (e.g., a Universal Serial Bus (USB) port). In further related aspects, the apparatus 1000 may optionally include a module for storing information, such as, for example, a memory device 1016. The computer readable medium or the memory module 1016 may be operatively coupled to the other components of the apparatus 1000 via the bus 1010 or the like. The memory module 1016 may be adapted to store computer readable instructions and data for effecting the processes and behavior of the modules 1002-1005, and subcomponents thereof, or the processor 1010, or the method 900 and one or more of the additional operations disclosed herein. The memory module 1016 may retain instructions for executing functions associated with the modules 1002-1005. While shown as being external to the memory 1016, it is to be understood that the modules 1002-1005 can exist within the memory 1016 or an on-chip memory of the processor 1010.

The apparatus 1000 may include a transceiver (not shown) configured as a wireless transmitter/receiver, or a wired transmitter/receiver, for transmitting and receiving a communication signal to/from another system component such as, for example, a server or client device. In alternative embodiments, the processor 1010 may include networked microprocessors from devices operating over a computer network. In addition, the apparatus 1000 may include any suitable display output and user interface device for interaction with a user.

Figure 11:
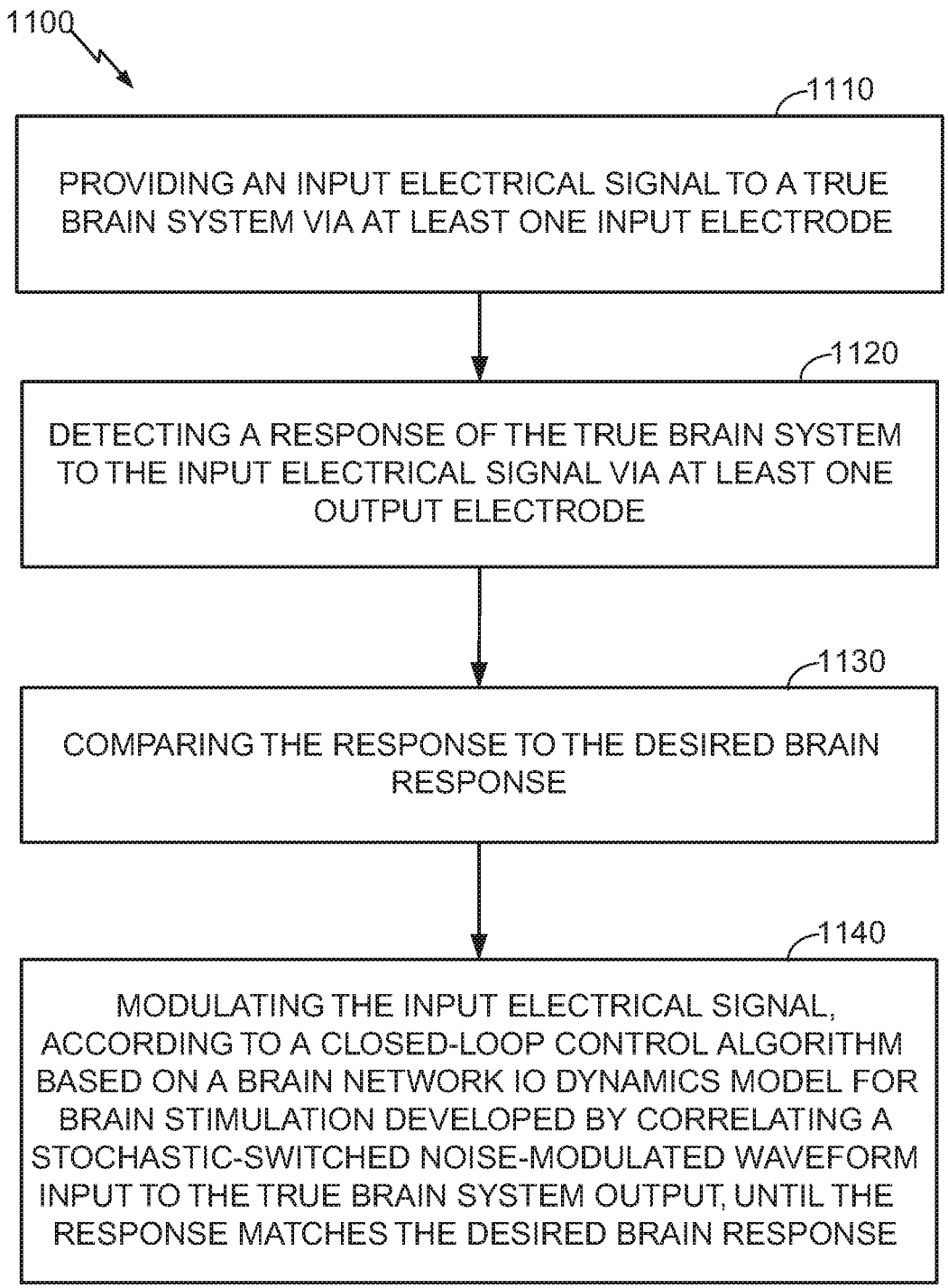
FIG. 11 is a flowchart illustrating aspects of a method for treatment of a neurological disorder using a closed-loop controller of stimulation constructed based on the noise-modulated waveform.

Referring to FIG. 11, a method 1100 for causing a desired brain response to an input electrical signal may include, at 1110, providing an input electrical signal to a true brain system via at least one input electrode. The method 1100 may further include, at 1120, detecting a response of the true brain system to the input electrical signal via at least one output electrode. The method may further include, at 1130, comparing the response to a desired brain response. The method 1100 may further include, at 1140, modulating the input electrical signal, according to a closed-loop control algorithm based on a brain network IO dynamics model for brain stimulation developed by correlating a stochastic-switched noise-modulated waveform input to the true brain system output, until the response matches the desired brain response.

In an aspect of the method 1100, the brain network IO dynamics model optimally correlates the input stochastic-switched noise-modulated waveform to the true brain system output, as described elsewhere herein. In one use case of the method 1100, the desired brain response mitigates a neuropathic condition, for example, Parkinson's disease, or depression. In another use case, the desired brain response heightens a brain performance parameter, for example, wakefulness, focus, or memory.

Figure 12:
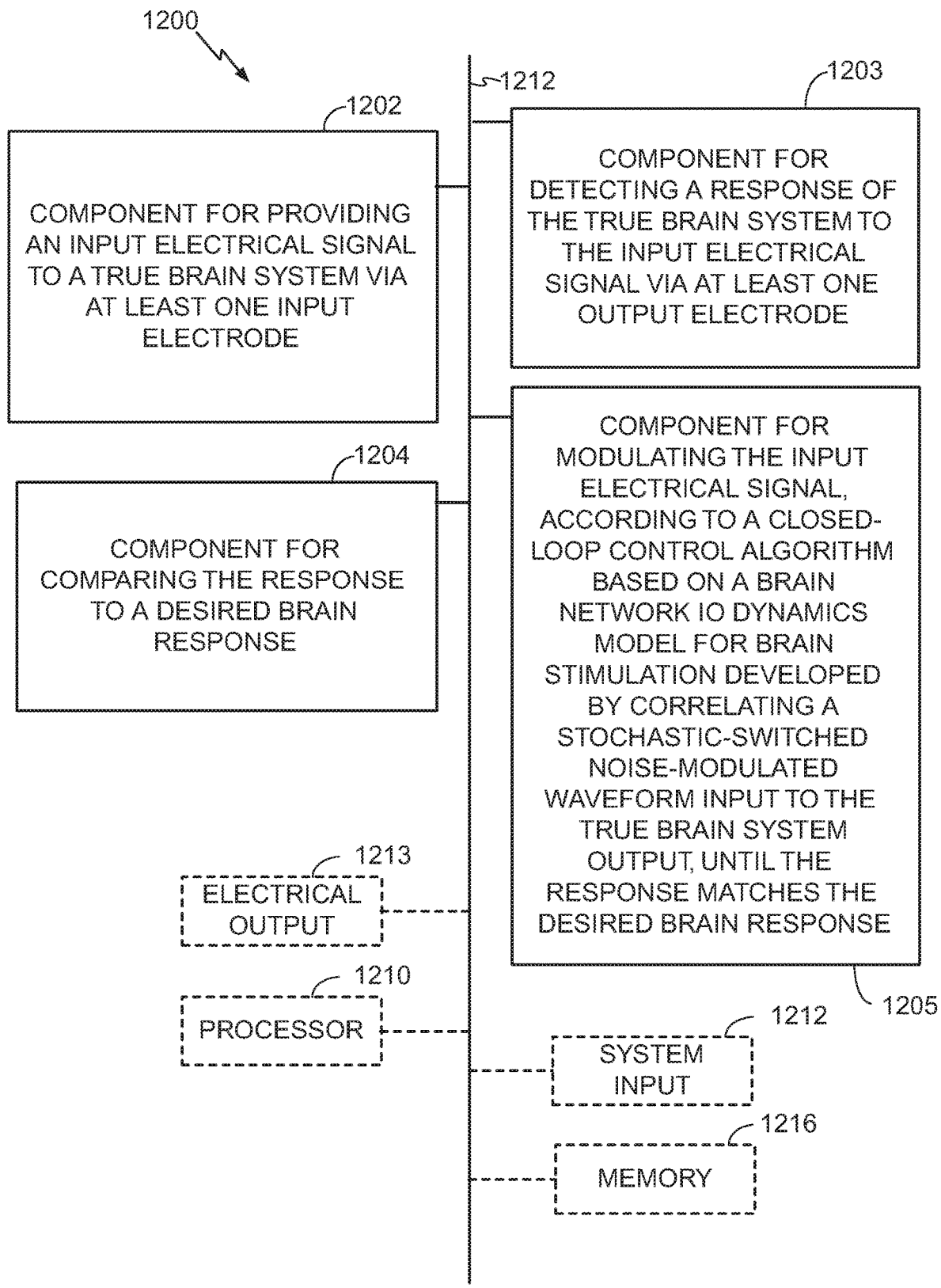
FIG. 12 is a block diagram illustrating aspects of an apparatus for performing the method shown in FIG. 11.

FIG. 12 is a conceptual block diagram illustrating components of an apparatus or system 1200 for causing a desired brain response to an input electrical signal. The apparatus or system 1200 may include additional or more detailed components for performing functions or process operations as described herein. As depicted, the apparatus or system 1200 may include functional blocks that can represent functions implemented by a processor, software, or combination thereof (e.g., firmware).

As illustrated in FIG. 12, the apparatus or system 1200 may comprise an electrical component 1202 for providing an input electrical signal to a true brain system via at least one input electrode. The component 1202 may be, or may include, a means for said providing. Said means may include the processor 1210 coupled to the memory 1216, and to an output of a sensor array (not shown), the processor executing an algorithm based on program instructions stored in the memory. Such algorithm may include a sequence of more detailed operations, for example, generating an initial waveform as a digital sequence, converting the waveform to an analog signal, correlating the output to a time index, and transmitting the analog signal from a output electrode 1213.

The apparatus 1200 may further include an electrical component 1203 for detecting a response of the true brain system to the input electrical signal via at least one output electrode. The component 1203 may be, or may include, a means for said detecting. Said means may include the processor 1210 coupled to the memory 1216, the processor executing an algorithm based on program instructions stored in the memory. Such algorithm may include a sequence of more detailed operations, for example, receiving an analog signal at an input 1212, correlating the input signal to a time index, and converting the signal to a digital sequence.

The apparatus 1200 may further include an electrical component 1204 for comparing the response to a desired brain response. The component 1204 may be, or may include, a means for said comparing. Said means may include the processor 1210 coupled to the memory 1216 and to a sensor (not shown), the processor executing an algorithm based on program instructions stored in the memory. Such algorithm may include a sequence of more detailed operations, for example, retrieving the time-indexed output and input sequences, and computing a difference over each correlated time interval.

The apparatus 1200 may further include an electrical component 1205 for modulating the input electrical signal, according to a closed-loop control algorithm based on a brain network IO dynamics model for brain stimulation developed by correlating a stochastic-switched noise-modulated waveform input to the true brain system output, until the response matches the desired brain response. The component 1205 may be, or may include, a means for said modulating. Said means may include the processor 1210 coupled to the memory 1216, the processor executing an algorithm based on program instructions stored in the memory. Such algorithm may include a sequence of more detailed operations, for example, applying a closed-loop control scheme based on an identified brain I/O system model as described more fully elsewhere herein.

The apparatus 1200 may optionally include a processor module 1210 having at least one processor. The processor 1210 may be in operative communication with the modules 1202-1205 via a bus 1212 or similar communication coupling. In the alternative, one or more of the modules may be instantiated as functional modules in a memory of the processor. The processor 1210 may effect initiation and scheduling of the processes or functions performed by electrical components 1202-1205.

In related aspects, the apparatus 1200 may include a network interface module (not shown) operable for communicating with system components over a computer network. A network interface module may be, or may include, for example, an Ethernet port or serial port (e.g., a Universal Serial Bus (USB) port). In further related aspects, the apparatus 1200 may optionally include a module for storing information, such as, for example, a memory device 1216. The computer readable medium or the memory module 1216 may be operatively coupled to the other components of the apparatus 1200 via the bus 1212 or the like. The memory module 1216 may be adapted to store computer readable instructions and data for effecting the processes and behavior of the modules 1202-1205, and subcomponents thereof, or the processor 1210, or the method 1100 and one or more of the additional operations disclosed herein. The memory module 1216 may retain instructions for executing functions associated with the modules 1202-1205. While shown as being external to the memory 1216, it is to be understood that the modules 1202-1205 can exist within the memory 1216 or an on-chip memory of the processor 1210.

The apparatus 1200 may include a transceiver (not shown) configured as a wireless transmitter/receiver, or a wired transmitter/receiver, for transmitting and receiving a communication signal to/from another system component such as, for example, a server or client device. In alternative embodiments, the processor 1210 may include networked microprocessors from devices operating over a computer network. In addition, the apparatus 1200 may include any suitable display output and user interface device for interaction with a user.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component", "module", "system", and the like are intended to refer to a computer-related entity, either hardware, a combination of hardware and software, software, or software in execution. For example, a component or a module may be, but are not limited to being, a process running on a processor, a processor, an object, an executable, a thread of execution, a program, and/or a computer. By way of illustration, both an application running on a server and the server can be a component or a module. One or more components or modules may reside within a process and/or thread of execution and a component or module may be localized on one computer and/or distributed between two or more computers.

Various aspects will be presented in terms of systems that may include a number of components, modules, and the like. It is to be understood and appreciated that the various systems may include additional components, modules, etc. and/or may not include all of the components, modules, etc. discussed in connection with the figures. A combination of these approaches may also be used. The various aspects disclosed herein can be performed on electrical devices including devices that utilize touch screen display technologies, heads-up user interfaces, wearable interfaces, and/or mouse-and-keyboard type interfaces. Examples of such devices include VR output devices (e.g., VR headsets), AR output devices (e.g., AR headsets), computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, digital versatile disk (DVD), Blu-ray™, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a client device or server. In the alternative, the processor and the storage medium may reside as discrete components in a client device or server.

Furthermore, the one or more versions may be implemented as a method, apparatus, or article of manufacture using known programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips, or other format), optical disks (e.g., compact disk (CD), DVD, Blu-ray™ or other format), smart cards, and flash memory devices (e.g., card, stick, or other format). Of course, those skilled in the art will recognize many modifications may be made to this configuration without departing from the scope of the disclosed aspects.

In view of the exemplary systems described supra, methods that may be implemented in accordance with the disclosed subject matter have been described with reference to several flow diagrams. While for purposes of simplicity of explanation, the methods are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein. Additionally, it should be further appreciated that computer-executable instructions for the methods disclosed herein are capable of being stored on an article of manufacture to facilitate transporting and transferring such instructions to computers, which by executing the instructions are caused to perform the methods.

CONCLUSIONS

A novel computational framework is used to model and identify input-output dynamics of brain networks in response to electrical stimulation, with the goal of designing closed-loop controlled DBS systems. A new clinical simulation testbed using the Neuro Omega™ microelectrode recording and stimulation system to validate the framework is also developed. The computational framework consists of a novel input DBS/stimulation waveform—a pulse train with binary noise (BN)-modulated parameters to accurately identify the input-output dynamics with a linear state-space model. This input is extended to generalized binary noise (GBN)-modulated pulse trains to enable time-efficient identification; this is done by further estimating the time-constant of the underlying brain network using on-off stimulation. Performance of the framework was evaluated within the clinical simulation testbed by performing two sets of experiments while incorporating noise, unknown disturbances and stimulation artifacts. First, open-loop identification experiments using the (G)BN-modulated DBS/stimulation waveform demonstrated that the new input DBS/stimulation waveform was critical in accurate model identification. Second, closed-loop control experiments using the (G)BN-identified models demonstrated that the BN-identification framework was essential for accurate closed-loop control; in this case the treatment of depression serves as a non-limiting example. Results and methods have significant implications for the development of closed-loop DBS/stimulation systems or BMIs for future stimulation-based treatments of a wide range of neurological disorders including various neuropsychiatric disorders.

Having thus described embodiments of methods and apparatus for making use of a stochastic-switched waveform for identification of I/O brain network dynamics, it should also be appreciated that various modifications, adaptations, and alternative embodiments thereof may be made within the scope and spirit of the present invention. For example, use of a binary noise signal has been disclosed, but the inventive concepts described above would be equally applicable to implementations using other stochastically-switched waveforms that are not binary.

The invention claimed is:

1. A method for time-efficient identification of a brain network input-output (IO) dynamics model for brain stimulation, comprising:
   generating, by a waveform generator, an input stochastic-switched noise-modulated waveform characterized by at least one parameter modulated according to a stochastic-switched noise sequence;
   inputting the input stochastic-switched noise-modulated waveform to at least one electrode of a clinical brain-response system;
   recording by a processor coupled to a memory, one or more time-correlated outputs of the clinical brain-response system responsive to the input stochastic-switched noise-modulated waveform; and
   identifying, by the processor, as a brain network IO dynamics model for brain stimulation, a mathematical model that correlates the input stochastic-switched noise-modulated waveform to the one or more time-correlated outputs of the clinical brain-response system, wherein the correlation satisfies one or more optimality constraints,
   wherein the stochastic-switched noise-modulated waveform is generalized by a tunable parameter based on a ratio of a minimum switching time ($T_{sw}$) to a time constant ($T_c$) for the brain network IO model.

2. The method of claim 1, wherein the tunable parameter is determined by $1-T_{sw}/T_c$.

3. The method of claim 1, further comprising estimating a value of $T_c$ by applying an on-off input pattern to the clinical brain-response system in open loop mode and measuring a rise time for achieving a defined initial portion of a transition period.

4. The method of claim 3, wherein the defined initial portion is defined by $1/e$.

5. The method of claim 3, wherein the estimating further comprises repeating the applying and the measuring thereby obtaining multiple values of the rise time, and averaging the multiple values.

6. The method of claim 1, wherein the mathematical model is a linear state-space model.

7. The method of claim 1, wherein the clinical brain-response system is an electronic system that simulates brain response with the at least one electrode selected from a group consisting of microelectrodes and ECoG grids.

8. The method of claim 7, wherein the clinical brain-response system comprises a clinical microelectrode recording and stimulation system.

9. The method of claim 1, wherein the clinical brain-response system comprises an electrode implanted in a living brain with the outputs measured by an electrode array.

10. The method of claim 1, wherein the stochastic-switched noise-modulated waveform is a binary waveform.

11. The method of claim 1, wherein the at least one parameter is selected from frequency, amplitude, or pulse width.

* * * * *

UNITED STATES PATENT AND TRADEMARK OFFICE
CERTIFICATE OF CORRECTION

| | |
|---|---|
| PATENT NO. | : 11,399,773 B2 |
| APPLICATION NO. | : 16/325297 |
| DATED | : August 2, 2022 |
| INVENTOR(S) | : Maryam Shanechi |

It is certified that error appears in the above-identified patent and that said Letters Patent is hereby corrected as shown below:

In the Specification

Column 1 Line 13 insert:
--STATEMENT AS TO FEDERALLY SPONSORED RESEARCH
This invention was made with government support under contract number W911NF-14-2-0043 awarded by the Defense Advanced Research Projects Agency (DARPA). The government has certain rights in this invention.--

Signed and Sealed this
Twenty-fifth Day of October, 2022

*Katherine Kelly Vidal*

Katherine Kelly Vidal
*Director of the United States Patent and Trademark Office*